US011918334B2

(12) United States Patent
Thompson et al.

(10) Patent No.: US 11,918,334 B2
(45) Date of Patent: Mar. 5, 2024

(54) IMPEDANCE TRANSFORMATION MODEL FOR ESTIMATING CATHETER LOCATIONS

(71) Applicant: St. Jude Medical International Holding S.à.r.l., Luxembourg (LU)

(72) Inventors: Cable Thompson, St. Paul, MN (US); Anthony D. Hill, Minneapolis, MN (US); Silvina Rybnikov, Zichron Ya'Acov (IL); Yuriy Malinin, Edina, MN (US)

(73) Assignee: ST JUDE MEDICAL INTERNATIONAL HOLDING, SA.R.L., Luxembourg (LU)

( * ) Notice: Subject to any disclaimer, the term of this patent is extended or adjusted under 35 U.S.C. 154(b) by 189 days.

(21) Appl. No.: 16/667,079

(22) Filed: Oct. 29, 2019

(65) Prior Publication Data

US 2020/0138330 A1    May 7, 2020

Related U.S. Application Data

(60) Provisional application No. 62/756,931, filed on Nov. 7, 2018.

(51) Int. Cl.
*A61B 5/0538* (2021.01)
*A61B 5/00* (2006.01)
(Continued)

(52) U.S. Cl.
CPC ............ *A61B 5/0538* (2013.01); *A61B 5/062* (2013.01); *A61B 5/6833* (2013.01); *A61B 2018/00875* (2013.01)

(58) Field of Classification Search
CPC .................. A61B 5/062; A61B 5/6833; A61B 2018/00875; A61B 2034/2051; A61B 34/20; A61B 5/063; A61B 5/0538
See application file for complete search history.

(56) References Cited

U.S. PATENT DOCUMENTS 6,104,944 A    8/2000  Martinelli
6,233,476 B1   5/2001  Strommer et al.
(Continued)

FOREIGN PATENT DOCUMENTS

CN    1903122 A    1/2007
CN    101449292 A    6/2009
(Continued)

OTHER PUBLICATIONS

"Regularization (mathematics)", Oct. 29, 2018, 11 pages.
(Continued)

*Primary Examiner* — Nathan J Jenness
*Assistant Examiner* — Severo Antonio P Lopez
(74) *Attorney, Agent, or Firm* — Billion & Armitage

(57) ABSTRACT

Systems and methods are described herein for use in predicting impedance values or responses in a three-dimensional space. Broadly, an impedance potential field and its measurement characteristics is modeled in an impedance model such that an impedance measurement may be estimated for any location within the impedance potential field. The impedance model may evolve over time based on actual impedance measurements of electrodes located in the three-dimensional space. Initially a plurality of patch electrodes to provide an impedance field to a three-dimensional space while electrodes disposed in the impedance field measure impedances. While each patch is driven, a number of independent impedance fields exist between the non-driven patches. These independent impedance potential fields may be estimated and mapped to impedance measurements of the electrode(s) at locations(s) within the impedance field to model the impedance field.

18 Claims, 16 Drawing Sheets

(51) Int. Cl.
*A61B 5/06* (2006.01)
*A61B 18/00* (2006.01)

(56) References Cited

U.S. PATENT DOCUMENTS

| | | |
|---|---|---|
| 7,197,354 B2 | 3/2007 | Sobe |
| 7,263,397 B2 | 8/2007 | Hauck et al. |
| 7,386,339 B2 | 6/2008 | Strommer et al. |
| 7,536,218 B2 | 5/2009 | Govari et al. |
| 8,744,599 B2 | 6/2014 | Tegg |
| 2007/0060833 A1 | 3/2007 | Hauck |
| 2007/0073179 A1* | 3/2007 | Afonso ............ A61B 5/316 600/523 |
| 2007/0268287 A1 | 11/2007 | Magnin et al. |
| 2008/0161681 A1 | 7/2008 | Hauck |
| 2009/0205403 A1 | 8/2009 | Boese et al. |
| 2011/0105897 A1* | 5/2011 | Kornblau ......... A61B 5/0538 600/436 |
| 2011/0158488 A1 | 6/2011 | Cohen et al. |
| 2011/0176746 A1 | 7/2011 | Bucki et al. |
| 2011/0313414 A1 | 12/2011 | Liu et al. |
| 2012/0004533 A1 | 1/2012 | Peng et al. |
| 2012/0172702 A1 | 7/2012 | Koyrakh et al. |
| 2012/0265054 A1 | 10/2012 | Olson |
| 2012/0302869 A1 | 11/2012 | Koyrakh et al. |
| 2013/0066193 A1* | 3/2013 | Olson ............... A61B 5/063 600/424 |
| 2013/0211206 A1 | 8/2013 | Sands et al. |
| 2013/0267835 A1 | 10/2013 | Edwards |
| 2014/0221803 A1 | 8/2014 | Bar-Tal et al. |
| 2014/0275957 A1 | 9/2014 | Lupotti |
| 2016/0367168 A1* | 12/2016 | Malinin ............. A61B 5/066 |

FOREIGN PATENT DOCUMENTS

| | | | |
|---|---|---|---|
| CN | 103025242 A | 4/2013 | |
| CN | 103687533 A | 3/2014 | |
| CN | 103813748 A | 5/2014 | |
| CN | 104290730 A | 1/2015 | |
| EP | 2168478 A1 | 3/2010 | |
| EP | 2233070 B1 * | 2/2012 | ........ A61B 5/0538 |
| JP | 2007021218 A | 2/2007 | |
| JP | 2014064922 A * | 4/2014 | ........ A61B 5/0538 |
| JP | 2014511737 A | 5/2014 | |
| JP | 2014530030 A | 11/2014 | |
| JP | 2018519046 A | 7/2018 | |
| WO | 2007135609 A2 | 11/2007 | |
| WO | 2012001365 A1 | 1/2012 | |
| WO | 2012141775 A1 | 10/2012 | |
| WO | 2013039564 A2 | 3/2013 | |
| WO | 2014028114 A1 | 2/2014 | |
| WO | 2015085011 A1 | 6/2015 | |
| WO | 2016205807 A1 | 12/2016 | |
| WO | 2016205809 A1 | 12/2016 | |

OTHER PUBLICATIONS

Bourmaud, Guillaume, et al., "From Intrinsic Optimization to Iterated Extended Kalman Filtering on Lie Groups", J Math Imaging Vis, Jan. 2, 2016, 284-303.

Karlgaard, Christopher D, "Nonlinear Regression Huber—Kalman Filtering and Fixed-Interval Smoothing", Journal of Guidance, Control, and Dynamics, Jan. 8, 2015, 9 pages.

"Communication Pursuant to Article 94(3) EPC dated Sep. 20, 2022", 8 Pages.

"Notice of Reasons for Rejection dated Sep. 20, 2022", 3 Pages.

* cited by examiner

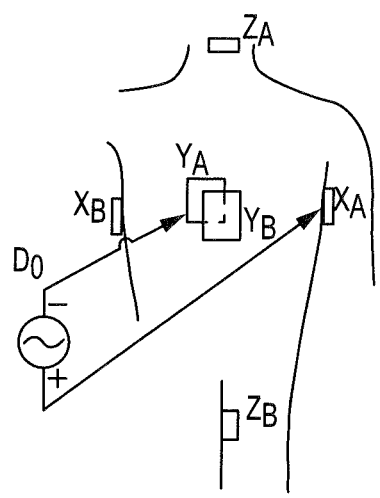
FIG.3A
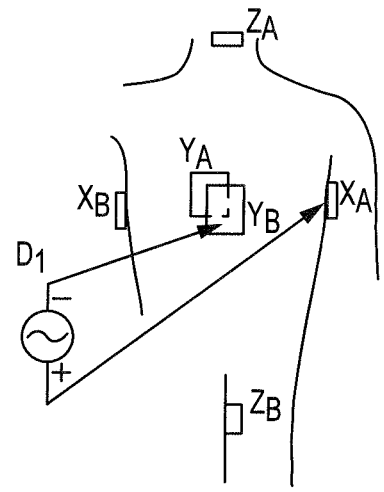
FIG.3B
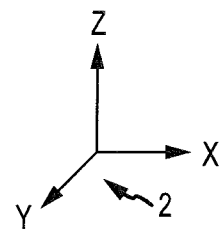
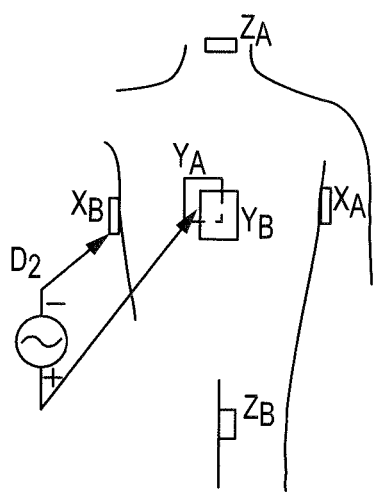
FIG.3C
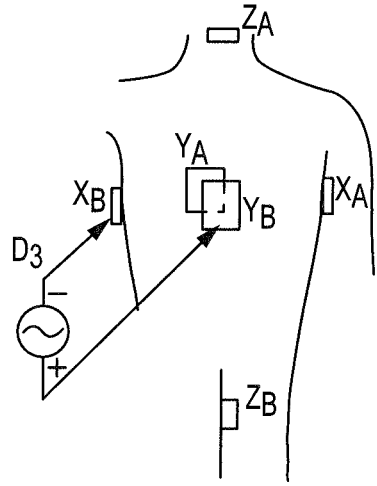
FIG.3D

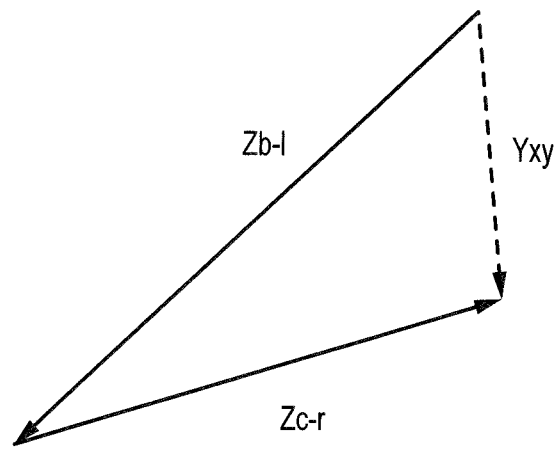
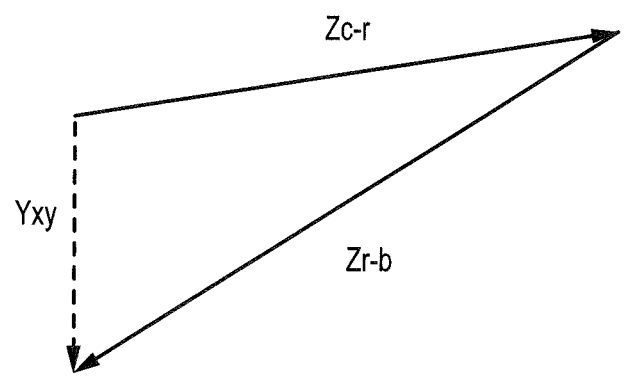
FIG.7B

IMPEDANCE TRANSFORMATION MODEL FOR ESTIMATING CATHETER LOCATIONS

The present application claims the benefit of the filing date of U.S. Provisional Application No. 62/756,931 having a filing date of Nov. 7, 2018, the entire contents of which are incorporated herein by reference.

BACKGROUND a. Field

The present disclosure relates generally to locating a medical device in a patient reference frame using a medical device model that estimates the shape of a medical device in the patient frame of reference in conjunction with measurements from impedance electrodes and magnetic sensors of the medical device.

b. Background

Various systems are known for determining the position and orientation (P&O) of a medical device in a human body, for example, for visualization and navigation purposes. One such system is known as an electrical impedance-based positioning system. Electrical impedance-based systems generally include one or more pairs of body surface electrodes (e.g., patches) outside a patient's body, a reference sensor (e.g., another patch) attached to the patient's body, and one or more sensors (e.g., electrodes) attached to the medical device. The pairs can be adjacent, linearly arranged, or associated with respective axes of a coordinate system for such a positioning system. The system can determine P&O by applying a current across pairs of electrodes, measuring respective voltages induced at the device electrodes (i.e., with respect to the reference sensor), and then processing the measured voltages.

Another system is known as a magnetic field-based positioning system. This type of system generally includes one or more magnetic field generators attached to or placed near the patient bed or other component of the operating environment and one or more magnetic field detection coils coupled with a medical device. Alternatively, the field generators may be coupled with a medical device, and the detection coils may be attached to or placed near a component of the operating environment. The generators provide a controlled low-strength AC magnetic field in the area of interest (i.e., an anatomical region). The detection coils produce a respective signal indicative of one or more characteristics of the sensed field. The system then processes these signals to produce one or more P&O readings associated with the coils (and thus with the medical device). The P&O readings are typically taken with respect to the field generators, and thus the field generators serve as the de facto "origin" of the coordinate system of a magnetic field-based positioning system. Unlike an electrical impedance-based system, where the coordinate system is relative to the patient on which the body surface electrodes are applied, a magnetic field-based system has a coordinate system that is independent of the patient.

Both electrical impedance-based and magnetic field-based positioning systems provide advantages. For example, electrical impedance-based systems provide the ability to simultaneously locate (i.e., provide a P&O reading for) a relatively large number of sensors on multiple medical devices. However, because electrical impedance-based systems employ electrical current flow in the human body, such systems may be subject to electrical interference. As a result, geometries and representations that are rendered based on position measurements may appear distorted relative to actual images of subject regions of interest. Magnetic field-based coordinate systems, on the other hand, are not dependent on characteristics of the patient's anatomy and typically provide improved accuracy. However, magnetic field-based positioning systems are generally limited to tracking relatively fewer sensors.

Efforts have been made to provide a system that combines the advantages of an electrical impedance-based positioning system (e.g., positioning of numerous electrodes) with the advantages of a magnetic-field based coordinate system (e.g., independence from patient anatomy, higher accuracy). In an embodiment, such a system may be provided by registering the coordinate systems of an electrical impedance-based positioning system with the coordinate system of a magnetic field-based positioning system. In such an arrangement, locations of electrodes may be identified in an impedance-based coordinate system in conjunction with identifying the locations of one or more magnetic sensors in a magnetic-based coordinate system. In an embodiment, at least a portion of the electrodes and magnetic sensors may be co-located to define fiducial pairs. This co-location allows for determining a transformation (e.g., transformation matrix) between the coordinate systems. The transformation may be applied to the locations of any electrode to register these locations in the magnetic-based coordinate system once the transformation is determined. Accordingly, the electrical impedance-based electrodes can be identified in the coordinate system of the magnetic field-based positioning system thereby increasing the positioning accuracy for the electrodes. While providing improved electrode positioning, the determination of a transformation between the impedance-based coordinate system and the magnetic based impedance system and subsequent registration of the electrode locations to the magnetic coordinate system can fail to account for various impedance shifts and/or drifts, associated with the electrode(s).

The previous systems that utilize electrode information (e.g., impedance measurements) and magnetic sensor information to provide improved electrode positioning in three-dimensional space (e.g., within a body of a patient) rely primarily on impedance-based measurements. That is, the magnetic sensor information (e.g., magnetic sensor measurements) delivers additional accuracy. This may be described as an impedance-primary location arrangement. Due to the distortion and temporal instability of the impedance measurements, such an arrangement can suffer from instability. Further, the previous impedance-primary location arrangements, in some instances, fail to account for various errors within the system. Further, such systems may fail to take into account other system inputs (e.g., patient movement, shape of the medical device, etc.), which may affect the calculated locations or positions of the electrodes. In summary, registration of an impedance-based system to magnetic-based system may fail to include additional information which may be observed and/or inferred and which may improve the overall identification of catheter and/or electrode positions in a three-dimensional space.

BRIEF SUMMARY OF THE INVENTION

Various embodiments described herein provide systems, methods and/or non-transitory computer readable medium storing instructions (i.e., utilities) for use in predicting impedance values or measurements in a three-dimensional space. Broadly, the utilities define an impedance potential field and its measurement characteristics such that an impedance measurement may be estimated for any location within the potential field. The utilities define a transformation or impedance model that estimates electrode impedance measurements in the three-dimensional space (e.g., location-to-impedance-values). The model may evolves over time based on actual impedance measurements of electrodes located in the three-dimensional space. The utilities utilize a plurality of patch electrodes to provide an impedance field to a three-dimensional space (e.g., a patient reference frame). For instance, such patch electrodes may be applied externally (e.g., surface patch electrodes) to a patient body. Individual pairs of the surface patch electrodes may be driven (e.g., source-sink) to generate an impedance field within the three-dimensional space. For instance, in a six-patch electrode system, six individual combinations of pairs of patch electrodes may be driven for each impedance measurement. One or more electrodes disposed in the impedance field may measure impedances while the various pairs patches are driven. In addition, for each set of driven patch pairs, a number of independent impedance fields exist between the non-driven patch pairs. That is, the non-driven patch pairs define independent impedance potential fields within the system. These independent impedance potential fields may be estimated and mapped to impedance measurements of the electrode(s) at locations(s) within the impedance field to define the impedance field. Such mapping of the independent impedance potentials to the measured impedances defines the model of the impedance field.

Once the impedance model is defined, impedance values may be predicted for predicted locations of electrodes in the impedance field. In one arrangement, locations of electrodes of a catheter may be predicted in the three-dimensional space using a catheter model, which models the catheter as disposed within the three-dimensional space. In such an arrangement, an actual impedance measurement or value(s) may be obtained for the electrode. The measured impedance value(s) and predicted impedance value(s) may then be utilized to generate an updated impedance value and/or location for the electrode. Such an updated impedance value may have an improved accuracy compared to either the predicted value or the measured value. Additionally, the predicted value and the measured value may be utilized to update the impedance model. For instance, these values may update the definitions of the independent impedance fields.

In an arrangement, the independent impedance fields are defined as a combination of basis functions. In one specific arrangement, the impedance fields are defined as a linear combination of harmonic basis functions. The basis functions may include weighting factors that may be adjusted in a stochastic process. In a further arrangement, definitions of the independent impedance fields may further be constrained. In another arrangement, definitions of the independent impedance fields may include error terms. Such error terms may include a distant dependent modeling error and/or a respiration dependent modeling error.

In an embodiment, the utilities integrate (e.g., fuse) predicted values and measured values to refine the model. In an embodiment, the model is a variable models where parameters of the model are state variables. Such a variable system allows updating the various models based, in part, on the measured responses of the physical system. In such an embodiment, an estimator system may estimate latent (e.g., hidden) variables of the model to iteratively improve the correspondence of the model with the physical systems it represents. In an embodiment, the estimator is an extended Kalman filter.

The foregoing and other aspects, features, details, utilities, and advantages of the present invention will be apparent from reading the following description and claims, and from reviewing the accompanying drawings.

BRIEF DESCRIPTION OF THE DRAWINGS

FIGS. 3A-3D illustrate exemplary external impedance patch pairs suitable for use with the system of FIG. 2.

FIG. 7B illustrates an independent impedance potential field.

DETAILED DESCRIPTION

Figure 1:
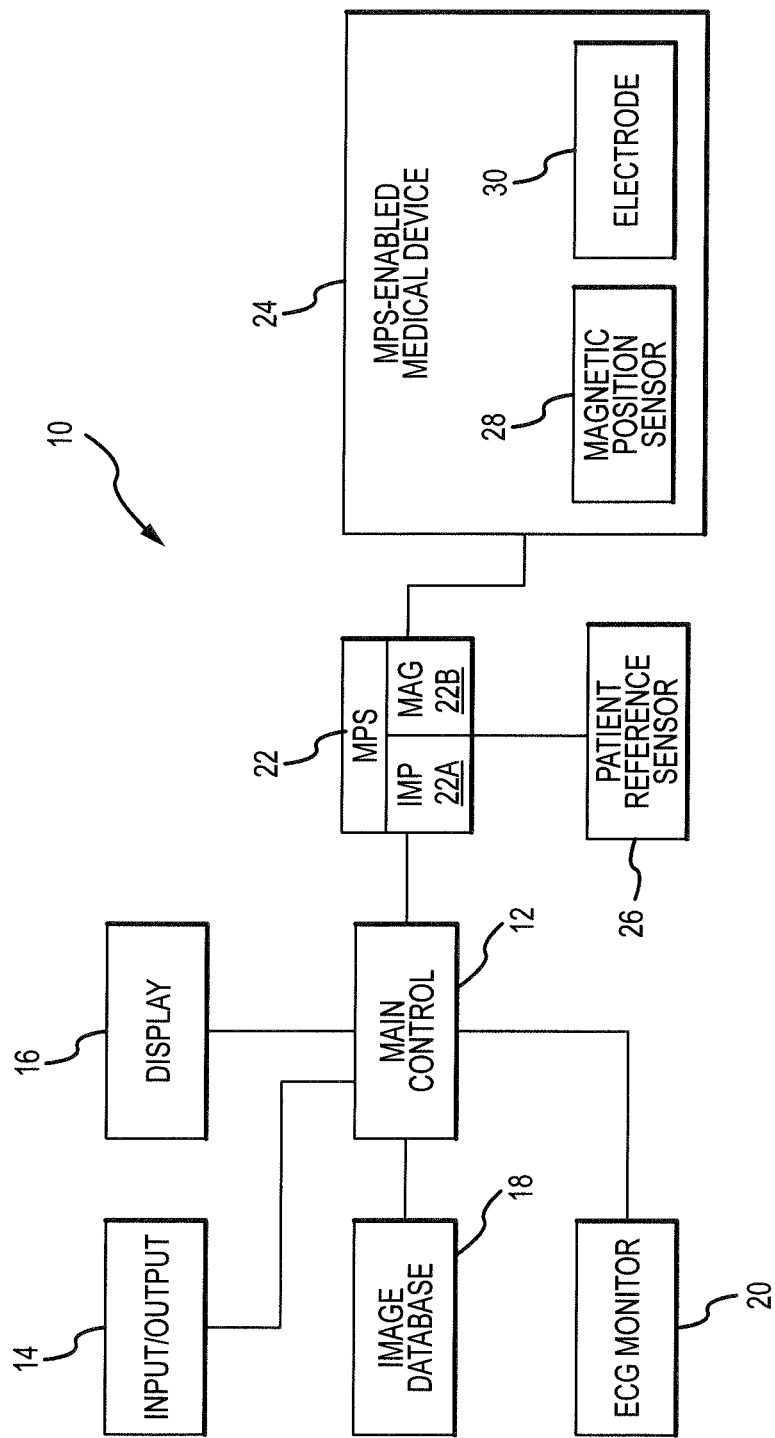
FIG. 1 illustrates a schematic block diagram view of a system for determining the position of a medical device using impedance and magnetic measurements.

Referring now to the drawings wherein like reference numerals are used to identify identical or similar components in the various views, FIG. 1 is a diagrammatic view of a system 10 in which a medical device, such as a guidewire, catheter, introducer (e.g., sheath) incorporating a magnetic position sensor 28 and an electrode 30 may be used.

Before proceeding to a detailed description of the embodiments of the present disclosure, a description of an exemplary environment in which such devices and sensors may be used will first be set forth. With continued reference to FIG. 1, system 10, as depicted, includes a main electronic control unit 12 (e.g., a processor) having various input/output mechanisms 14, a display 16, an optional image database 18, an electrocardiogram (ECG) monitor 20, a localization system, such as a medical positioning system 22, a medical positioning system-enabled elongate medical device 24, a patient reference sensor 26, magnetic position sensor(s) 28 and electrode(s) 30. For simplicity, one magnetic position sensor 28 and one electrode 30 are shown, however, more than one magnetic position sensor 28 and/or more than one electrode 30 can be included in the system 10.

Input/output mechanisms 14 may comprise conventional apparatus for interfacing with a computer-based control unit including, for example, one or more of a keyboard, a mouse, a tablet, a foot pedal, a switch and/or the like. Display 16 may also comprise conventional apparatus, such as a computer monitor.

Various embodiments described herein may find use in navigation applications that use real-time and/or pre-acquired images of a region of interest. Therefore system 10 may optionally include image database 18 to store image information relating to the patient's body. Image information may include, for example, a region of interest surrounding a destination site for medical device 24 and/or multiple regions of interest along a navigation path contemplated to be traversed by medical device 24. The data in image database 18 may comprise known image types including (1) one or more two-dimensional still images acquired at respective, individual times in the past; (2) a plurality of related two-dimensional images obtained in real-time from an image acquisition device (e.g., fluoroscopic images from an x-ray imaging apparatus), wherein the image database acts as a buffer (live fluoroscopy); and/or (3) a sequence of related two-dimensional images defining a cine-loop wherein each image in the sequence has at least an ECG timing parameter associated therewith, adequate to allow playback of the sequence in accordance with acquired real-time ECG signals obtained from ECG monitor 20. It should be understood that the foregoing embodiments are examples only and not limiting in nature. For example, the image database may also include three-dimensional image data as well. It should be further understood that the images may be acquired through any imaging modality, now known or hereafter developed, for example X-ray, ultra-sound, computerized tomography, nuclear magnetic resonance or the like.

ECG monitor 20 is configured to continuously detect an electrical timing signal of the heart organ through the use of a plurality of ECG electrodes (not shown), which may be externally-affixed to the outside of a patient's body. The timing signal generally corresponds to a particular phase of the cardiac cycle, among other things. Generally, the ECG signal(s) may be used by the control unit 12 for ECG synchronized play-back of a previously captured sequence of images (cine loop) stored in database 18. ECG monitor 20 and ECG-electrodes may both comprise conventional components.

Another medical positioning system sensor, namely, patient reference sensor (PRS) 26 (if provided in system 10) can be configured to provide a positional reference of the patient's body so as to allow motion compensation for patient body movements, such as respiration-induced movements. Such motion compensation is described in greater detail in U.S. patent application Ser. No. 12/650,932, entitled "Compensation of Motion in a Moving Organ Using an Internal Position Reference Sensor", hereby incorporated by reference in its entirety as though fully set forth herein. PRS 26 may be attached to the patient's manubrium sternum or other location. PRS 26 can be configured to detect one or more characteristics of the magnetic field in which it is disposed, wherein medical positioning system 22 determines a location reading (e.g., a P&O reading) indicative of the PRS's position and orientation in the magnetic reference coordinate system.

Medical positioning system 22 is configured to serve as the localization system and therefore to determine position (localization) data with respect to one or more magnetic position sensors 28 and/or electrodes 30 and output a respective location reading. In an embodiment, a medical positioning system 22 may include a first medical positioning system or an electrical impedance-based medical positioning system 22A that determines electrode locations in a first coordinate system, and a second medical positioning system or magnetic field-based medical positioning system 22B that determines magnetic position sensors in a second coordinate system. In an embodiment, the location readings may each include at least one or both of a position and an orientation (P&O) relative to a reference coordinate system (e.g., magnetic-based coordinate system or impedance-based coordinate system). For some types of sensors, the P&O may be expressed with five degrees-of-freedom (five DOF) as a three-dimensional (3D) position (e.g., a coordinate in three perpendicular axes X, Y and Z) and two-dimensional (2D) orientation (e.g., a pitch and yaw) of an electromagnetic position sensor 28 in a magnetic field relative to a magnetic field generator(s) or transmitter(s) and/or electrode 30 in an applied electrical field relative to an electrical field generator (e.g., a set of electrode patches). For other sensor types, the P&O may be expressed with six degrees-of-freedom (six DOF) as a 3D position (e.g., X, Y, Z coordinates) and 3D orientation (e.g., roll, pitch, and yaw).

Figure 2:
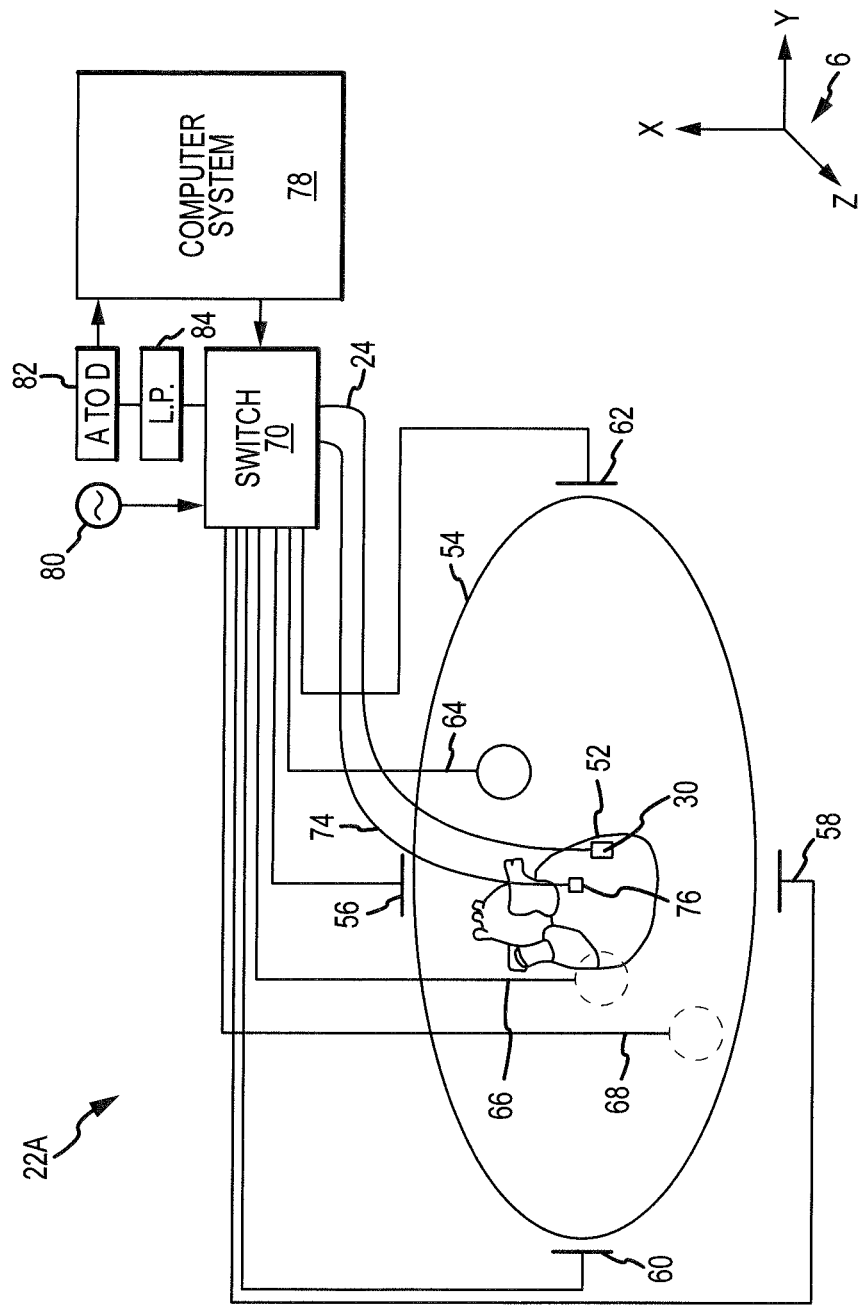
FIG. 2 illustrates a diagrammatic and block diagram view of an embodiment of an electrical impedance-based positioning system.

Impedance-based medical positioning system 22A determines electrode locations based on capturing and processing signals received from the electrodes 30 and external electrode patches while the electrodes are disposed in a controlled electrical field (e.g., potential field) generated by the electrode patches, for example. FIG. 2 is a diagrammatic overview of an exemplary electrical impedance-based medical positioning system ('MPS system') 22A. MPS system 22A may comprise various visualization, mapping and navigation components as known in the art, including, for example, an EnSite™ Electro Anatomical Mapping System commercially available from St. Jude Medical, Inc., or as seen generally by reference to U.S. Pat. No. 7,263,397 entitled "Method and Apparatus for Catheter Navigation and Location and Mapping in the Heart" to Hauck et al., or U.S. Patent Publication No. 2007/0060833 A1 to Hauck entitled "Method of Scaling Navigation Signals to Account for Impedance Drift in Tissue", both owned by the common assignee of the present invention, and both hereby incorporated by reference in their entireties.

Medical positioning system 22A includes a diagrammatic depiction of a heart 52 of a patient 54. The system includes the ability to determine a catheter electrode location (i.e., position and orientation) as the catheter distal end is moved around and within a chamber of the heart 52. For this purpose, three sets of body surface electrodes (patches) are shown: (1) electrodes 56, 58 (X-axis); (2) electrodes 60, 62 (Y-axis); and (3) electrodes 64, 66 (Z-axis). Additionally, a body surface electrode ("belly patch") 68 is shown diagrammatically. The surface electrodes are all connected to a switch 70. Of course, other surface electrode configurations and combinations are suitable for use with the present invention, including fewer electrodes, e.g., three electrodes, more electrodes, e.g., twelve, or different physical arrangements, e.g., linear arrangement instead of an orthogonal arrangement.

Medical device 24 is shown as a catheter with a distal electrode 30. Catheter 24 may have additional electrodes in addition to electrode 30 (e.g., a catheter tip electrode and/or ring electrodes) as well as one or more magnetic position sensors (not shown). FIG. 2 also shows a second, independent catheter 74 with a fixed reference electrode 76, which may be stationary on the heart for calibration purposes. In many instances, a coronary sinus electrode or other fixed reference electrode 76 in the heart 52 can be used as a reference for measuring voltages and displacements.

It should be understood that catheter 24 may include still other electrodes, and in other embodiments, such as in EP or RF ablation embodiments, the other electrodes may be used for any number of diagnostic and/or therapeutic purposes. For instance, such electrodes and therefore such catheters may be used for performing ablation procedures, cardiac mapping, electrophysiological (EP) studies and other diagnostic and/or therapeutic procedures. Embodiments are not limited to any one type of catheter or catheter-based system or procedure.

FIG. 2 further shows a computer system 78, a signal generator 80, an analog-to-digital converter 82 and a low-pass filter 84. Computer system 78 includes a processing apparatus configured to perform various functions and operations described herein. Computer system 78 may be configured to control signal generator 80 in accordance with predetermined strategies to selectively energize various pairs (dipoles) of surface electrodes. In operation, computer system 78 may (1) obtain raw patch data (i.e., voltage readings) via filter 84 and A-to-D converter 82 and (2) use the raw patch data in conjunction with electrode measurements) to determine the raw, uncompensated, electrode location coordinates of a catheter electrode positioned inside the heart or chamber thereof (e.g., such as electrode 30) in a three-dimensional coordinate system (e.g., impedance-based coordinate system). Computer system 78 may be further configured to perform one or more compensation and adjustment functions, and to output a location in coordinate system 14 of one or more electrodes such as electrode 76. Motion compensation may include, for example, compensation for respiration-induced patient body, movement, as described in U.S. patent application Ser. No. 12/980,515, entitled "Dynamic Adaptive Respiration Compensation with Automatic Gain Control", which is hereby incorporated by reference in its entirety.

Each body surface (patch) electrode is independently coupled to switch 70 and pairs of electrodes are selected by software running on computer system 78, which couples the patches to signal generator 80. A pair of electrodes, for example the Z-axis electrodes 64 and 66, may be excited by signal generator 80 to generate an electrical field in the body of patient 54 and heart 52. In one embodiment, this electrode excitation process occurs rapidly and sequentially as different sets of patch electrodes are selected and one or more of the unexcited (in an embodiment) surface electrodes are used to measure voltages. During the delivery of the excitation signal (e.g., current pulse), the remaining (unexcited) patch electrodes may be referenced to the belly patch 68 and the voltages impressed on these remaining electrodes are measured by the A-to-D converter 82. In this fashion, the surface patch electrodes are divided into driven and non-driven electrode sets. Low pass filter 84 may process the voltage measurements. The filtered voltage measurements are transformed to digital data by analog to digital converter 82 and transmitted to computer 78 for storage under the direction of software. This collection of voltage measurements is referred to herein as the "patch data." The software has access to each individual voltage measurement made at each surface electrode during each excitation of each pair of surface electrodes.

The patch data is used, along with measurements made at electrode 30, to determine a relative location of electrode 30 in what may be termed a patient-based coordinate system or patient reference frame 6. That is, as the patches are applied directly to the patient, the patient defines the reference frame of the impedance measurements. Potentials across each of the six orthogonal surface electrodes may be acquired for all samples except when a particular surface electrode pair is driven (in an embodiment). In one embodiment, sampling while a surface electrode acts as a source or sink in a driven pair is normally avoided as the potential measured at a driven electrode during this time may be skewed by the electrode impedance and the effects of high local current density. In an alternate embodiment, however, sampling may occur at all patches (even those being driven).

Generally, in one embodiment, three nominally orthogonal electric fields are generated by a series of driven and sensed electric dipoles in order to realize localization function of the catheter in a biological conductor. Alternately, these orthogonal fields can be decomposed and any pair of surface electrodes (e.g., non-orthogonal) may be driven as dipoles to provide effective electrode triangulation. FIGS. 3A-3D show a plurality of exemplary non-orthogonal dipoles, designated $D_0$, $D_1$, $D_2$ and $D_3$, set in the impedance-based coordinate system 2. In FIGS. 3A-3D, the X-axis surface electrodes are designated $X_A$ and $X_B$, the Y-axis surface electrodes are designated YA and YB, and the Z-axis electrodes are designated $Z_A$ and $Z_B$. For any desired axis, the potentials measured across an intra-cardiac electrode 30 resulting from a predetermined set of drive (source-sink) configurations may be combined algebraically to yield the same effective potential as would be obtained by simply driving a uniform current along the orthogonal axes. Any two of the surface electrodes 56, 58, 60, 62, 64, 66 (see FIG. 2) may be selected as a dipole source and drain with respect to a ground reference, e.g., belly patch 68, while the unexcited body surface electrodes measure voltage with respect to the ground reference. The measurement electrode 30 placed in heart 52 is also exposed to the field from a current pulse and is measured with respect to ground, e.g., belly patch 68. In practice, a catheter or multiple catheters within the heart may contain multiple electrodes and each electrode potential may be measured separately. As previously noted, alternatively, at least one electrode may be fixed to the interior surface of the heart to form a fixed reference electrode 76, which may also be measured with respect to ground.

Data sets from each of the surface electrodes and the internal electrodes are all used to determine the location of measurement electrode 30 within heart 52. After the voltage measurements are made, a different pair of surface electrodes is excited by the current source and the voltage measurement process of the remaining patch electrodes and internal electrodes takes place. The sequence occurs rapidly, e.g., on the order of 100 times per second in an embodiment. To a first approximation the voltage on the electrodes within the heart bears a linear relationship with position between the patch electrodes that establish the field within the heart, as more fully described in U.S. Pat. No. 7,263,397 referred to above.

Magnetic-based medical positioning system 22B determines magnetic position sensor locations (e.g., P&O) in a magnetic coordinate system based on capturing and processing signals received from the magnetic position sensor 28 while the sensor is disposed in a controlled low-strength alternating current (AC) magnetic (e.g., magnetic) field. Each magnetic position sensor 28 and the like may comprise a coil and, from an electromagnetic perspective, the changing or AC magnetic field may induce a current in the coil(s) when the coil(s) are in the magnetic field. The magnetic position sensor 28 is thus configured to detect one or more characteristics (e.g., flux) of the magnetic field(s) in which it is disposed and generate a signal indicative of those characteristics, which is further processed by medical positioning system 22B to obtain a respective P&O for the magnetic sensor 28 relative to, for example, a magnetic field generator.

Figure 4:
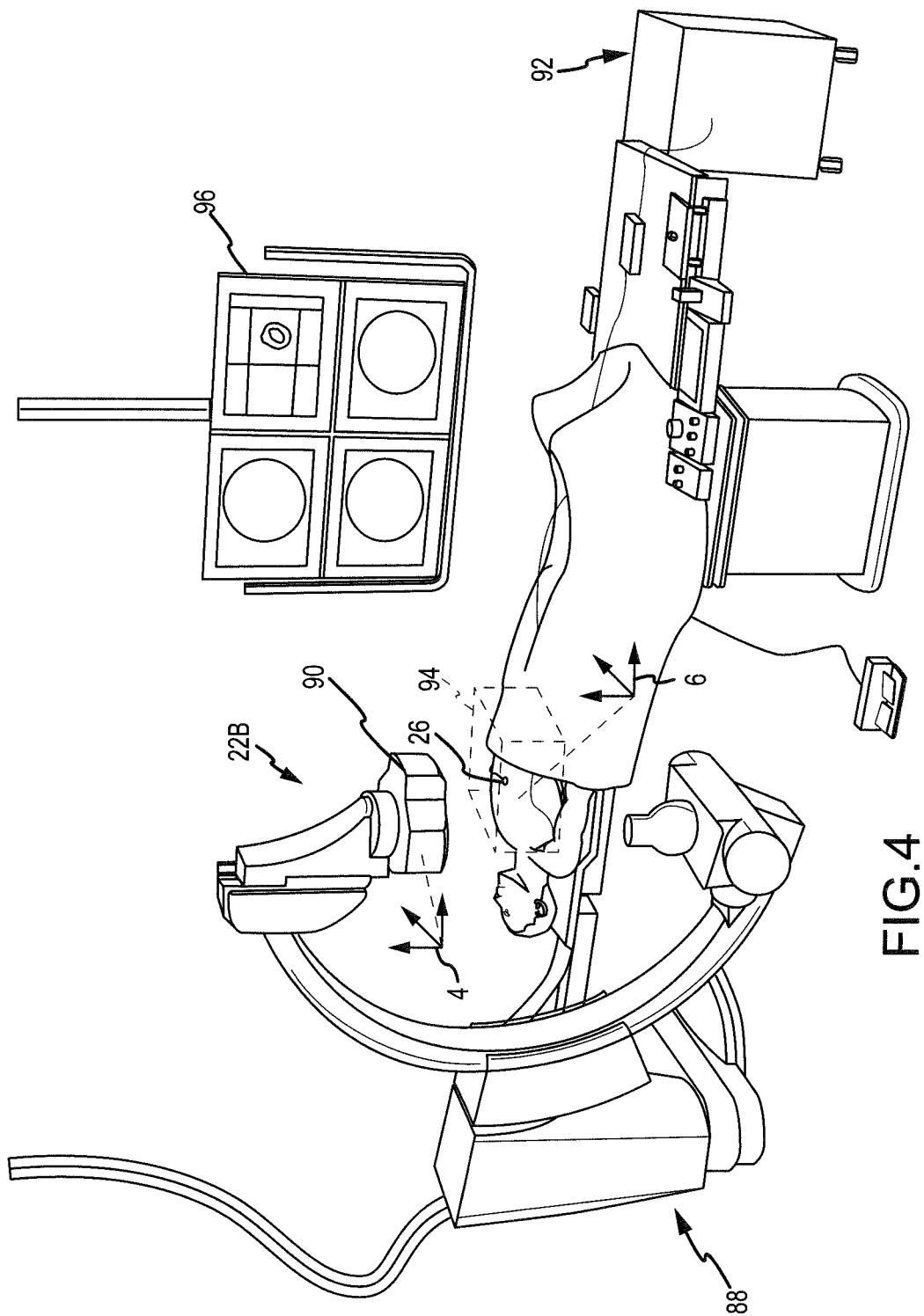
FIG. 4 illustrates an embodiment of a magnetic field-based positioning system.

FIG. 4 is a diagrammatic view of an exemplary magnetic field-based medical positioning system 22B in a fluoroscopy-based imaging environment, designated system 88. A magnetic field generator or magnetic transmitter assembly (MTA) 90 and a magnetic processing core 92 for determining position and orientation (P&O) readings generally define the magnetic field-based positioning system 22B. The MTA 90 is configured to generate the magnetic field(s) in and around the patient's chest cavity in a predefined three-dimensional space designated as motion box 94 in FIG. 4. Magnetic field sensors coupled with device 24 (e.g., catheter or another medical device) are configured to sense one or more characteristics of the magnetic field(s) and, when the sensors are in the motion box 94, each generates a respective signal that is provided to the magnetic processing core 92. The processing core 92 is responsive to these detected signals and is configured to calculate respective three-dimensional position and orientation (P&O) readings for each magnetic field sensor. Thus, the MPS system 22B enables real-time tracking of each magnetic field sensor in three-dimensional space, which forms a magnetic-based coordinate system 4. The position of the sensors may be shown on a display 96 relative to, for example only, a cardiac model or geometry. Additional exemplary embodiments of magnetic field-based medical positioning systems are set forth in co-owned U.S. Pat. No. 7,386,339 and U.S. Pat. App. No 2013/0066193, hereby incorporated by reference in their entirety. It should be understood that variations are possible, for example, as also seen by reference to U.S. Pat. Nos. 7,197,354, and 6,233,476, also hereby incorporated by reference in their entireties. Unlike the electrical impedance-based system discussed in relation to FIG. 2, which has an origin based on a patient reference frame 6 as the body surface electrodes are applied directly to the patient, the origin of the magnetic field-based system is typically based in or on the MTA 90 (e.g., as shown by the dashed line) and is independent of the patient. Stated otherwise, the patient coordinate system (e.g., patient reference frame) 6 and the magnetic-based coordinate system 4 have different origins.

As further illustrated in FIG. 4, a patient reference sensor (PRS) 26 may be applied to the patient. In an embodiment, the PRS 26 may be attached to the patient's manubrium sternum. However other patient locations for the PRS 26 are possible. In an embodiment, the PRS 26 is a magnetic sensor configured to detect one or more characteristics of the magnetic field in which it is disposed, wherein medical positioning system 22B determines a location reading (e.g., a P&O reading) indicative of the position and orientation of the PRS 26 (e.g., in the magnetic-based coordinate system). For the present application, the PRS defines an origin (e.g., PRF 0,0,0) in the patient reference coordinate system or patient reference frame 6 (PRF). The origin may be offset from the actual location of the senor. That is, predetermined offsets (e.g., x, y, and z) may be applied to the PRS measurements that correspond with estimated distances between the sensor's placement on the patient and the desired origin. For instance, the origin may be offset from the sensor such that it is within the heart of the patient for cardiac applications. Further, two or more PRS may be applied to provide additional orientation information for the PRF 6. In any embodiment, as the PRS 26 is attached to the patient and moves with patient movement, the origin of the PRF 6 also moves. Such movement may result from patient respiration and/or physical movements (shifting, rolling etc.) of the patient. The origin of the PRF 6 is thus dependent on the position of the patient and may be updated over time. More specifically, a measurement of the PRS may be determined in the magnetic field coordinate system and this measurement may be utilized as the origin (e.g., with adjustment) of the PRF.

As previously noted, the impedance-based medical positioning systems and magnetic-based medical positioning systems have different strengths and weaknesses. For instance impedance-based systems provide the ability to simultaneously locate a relatively large number of electrodes. However, because impedance-based systems employ electrical current flow in the human body, the system can be subject to measurement inaccuracies due to shift and/or drift caused by various physiological phenomena (e.g., local conductivity changes, sweat/patch interactions, etc.). Additionally, impedance-based systems may be subject to electrical interference. As a result, electrode locations, renderings, geometries and/or representations based on such impedance-based measurements may be distorted. Magnetic-based systems, on the other hand, are not dependent on the characteristics of a patient's anatomy and are considered to provide a higher degree of accuracy. However, magnetic position sensors generally are limited to tracking relatively fewer sensors.

Previous efforts have been made to provide a system that combines the advantages of an electrical impedance-based positioning system (e.g., positioning of numerous electrodes) with the advantages of a magnetic-field based coordinate system (e.g., independence from patient anatomy, higher accuracy). In an embodiment, such a system may be provided by registering the coordinate systems of an electrical impedance-based positioning system with the coordinate system of a magnetic field-based positioning system. In such an arrangement, locations of electrodes may be identified in an impedance-based coordinate system in conjunction with the identifying the locations of one or more magnetic sensors in a magnetic-based coordinate system. In an embodiment, at least a portion of the electrodes and magnetic sensors may be co-located to define fiducial pairs. This co-location allows for determining a transformation (e.g., transformation matrix) between the coordinate systems. The transformation may be applied to the locations of any electrode to register these locations in the magnetic-based coordinate system once the transformation is determined. Accordingly, the electrical impedance-based electrodes can be identified in the coordinate system of the magnetic field-based positioning system thereby increasing the positioning accuracy for the electrodes. Such a system is set forth in co-owned U.S. Pat. Pub. No. 2013/0066193. The previous efforts that utilize electrode information (e.g., impedance measurements) and magnetic sensor information to provide improved electrode positioning in three-dimensional space (e.g., within a body of a patient), in some instances, fail to account for various errors within the system. By way of example, a transformation between the impedance-based coordinate system and the magnetic-based impedance system may underestimate error or uncertainty in the electrode and/or magnetic sensor measurements. Further, registration of an impedance-based system to magnetic-based system may fail to include additional information which may be observed and/or inferred and which may improve the overall identification of catheter and/or electrode positions in a three-dimensional space.

To provide an improved system for determining the location of electrodes in three-dimensional space such as within a body of a patient, the present disclosure is in part directed to a location arrangement (e.g., sensor fusion process or algorithm) that continuously integrates (e.g., fuses) impedance measurements from the electrodes and external patches with position and orientation measurements from magnetic sensors to estimate the latent state (e.g., position) of a medical device disposed within a patient reference frame. The latent state is used to track catheter electrodes within a body of a patient as though there were a magnetic sensor located at each catheter electrode, thereby achieving both accuracy and stability. More broadly, the presented arrangement expands the number of observed parameters utilized to locate the electrodes within a patient reference frame without relying on direct transformation between the impedance-based coordinate system and the magnetic-based impedance coordinate system based on the existence of fiducial pairs of electrodes and sensors. Rather, the impedance measurements and magnetic measurements are utilized as inputs to an overall system model that estimates/predicts and updates catheter electrode locations in a patient reference frame.

Figure 5A:
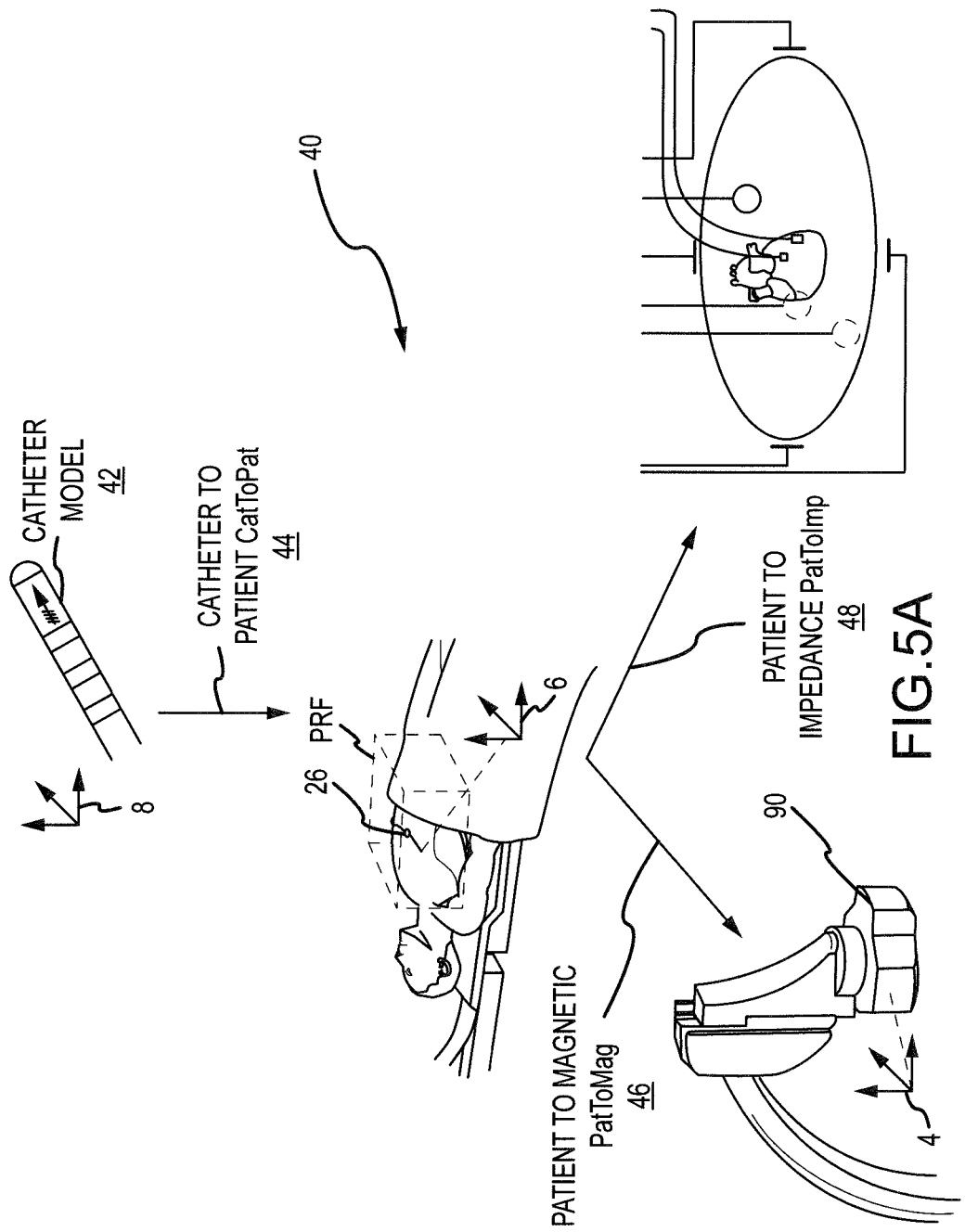
FIG. 5A illustrates a set of models utilized for describing a composite model in accordance with the disclosure.

FIG. 5A illustrates an embodiment of independent models that are used to mathematically define a catheter and/or electrode location system model. That is, the independent models define a composite model 40 of the system (e.g., in the patient reference frame). The illustrated embodiment of the composite system model 40 includes four models: a catheter model 42 (e.g., medical device model) that predicts the shape (e.g., catheter configuration) of a catheter having one or more electrodes and/or magnetic sensors in a catheter frame of reference 8, a catheter position and orientation model 44 that transforms the catheter model from the catheter reference frame 8 into the patient reference frame 6 based on a unique transformation that is specific to the catheter, a magnetic model 46 that predicts magnetic sensor measurements in the patient reference frame, and an impedance model 48 that predicts electrode impedance measurements in the patient reference frame. Each model mathematically describes a portion of the overall system.

Figure 5B:
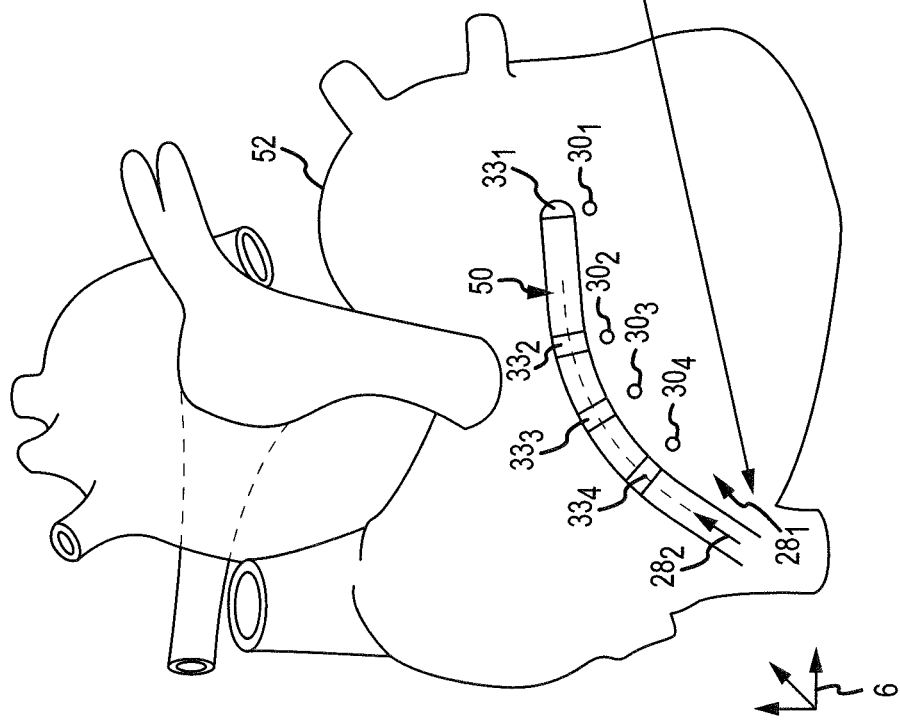
FIG. 5B illustrates a prediction of a catheter shape and translation of the catheter shape to a patient reference frame.
Figure 5C:
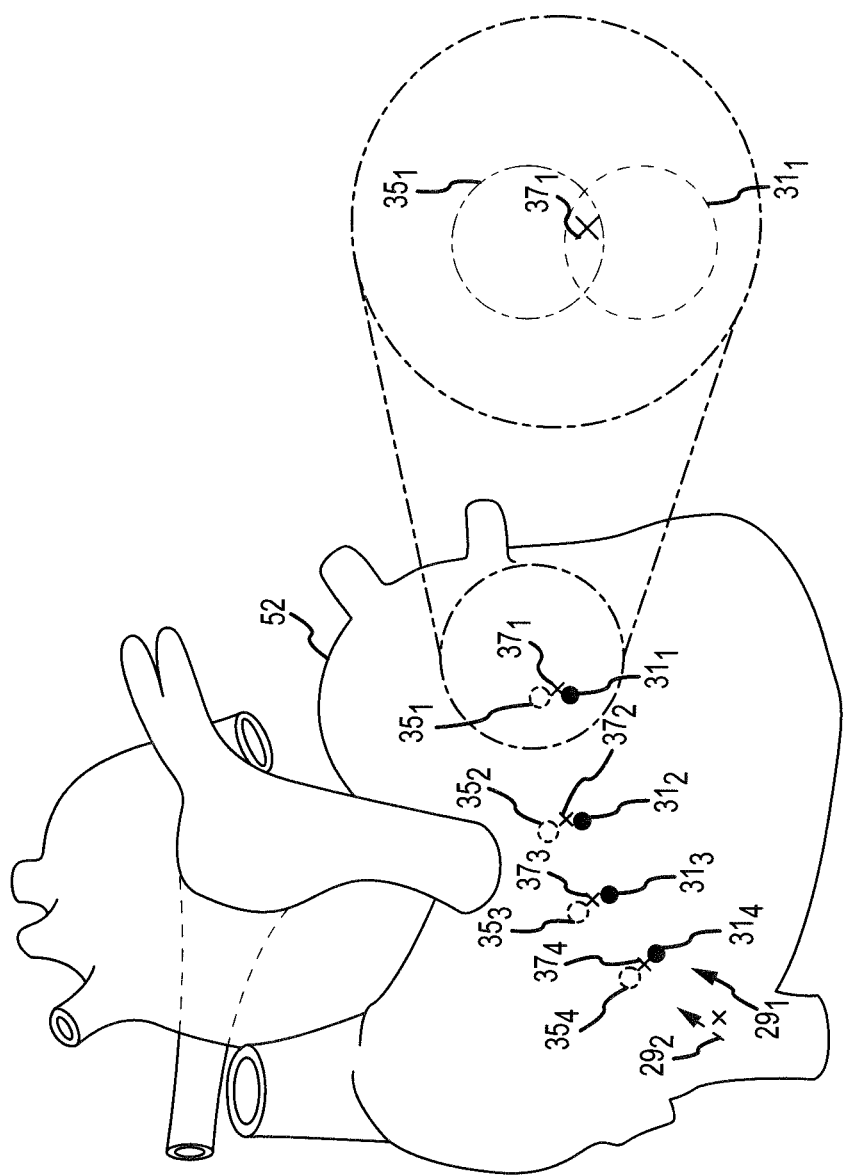
FIG. 5C illustrates the prediction of measurements for predicted locations in a patient reference frame and observed measurements in the patient reference frame.

FIG. 5B further illustrates the cooperation of the various models. Initially, the catheter model 42 predicts a catheter shape of a corresponding physical catheter 50 disposed within a three-dimensional space such as a body of a patient (e.g., heart 52), where the physical catheter 50 has a set of electrode $33_1$-$33_4$ and a magnetic sensor $28_2$. In the illustrated embodiment, the catheter shape includes model positions or locations of model electrodes $30_1$-$30_4$ and a model magnetic sensor $28_1$ (i.e., which correspond to the physical electrode $33_1$-$33_4$ and magnetic sensor $28_2$) in the catheter reference frame 8. A position and orientation model 44 applies one or more transformations to the catheter model 42 to translate the model from the catheter reference frame 8 to the patient reference frame 6. Upon transformation, locations of the model electrodes $30_1$-$30_4$ and/or model magnetic sensor $28_1$ are predicted in the patient reference frame 6, as illustrated by the solid circles for the electrodes $30_1$-$30_4$ and the vector for the magnetic sensor $28_1$ as shown located in the patient heart 52. The impedance model 48 predicts impedance measurements $31_1$-$31_4$ for the predicted electrode locations of the model electrodes $30_1$-$30_4$ in the patient reference frame while the magnetic model 46 predicts a location for the model sensor $28_1$ in the patient reference frame. This is illustrated in FIG. 5C where the predicted electrode responses (e.g., locations) $31_1$-$31_4$ for each predicted model electrode location are represented by solid dots and the predicted magnetic measurement $29_1$ for the model sensor $28_1$ is represented by the solid vector. The impedance-based medical positioning system measures actual responses $35_1$-$35_4$ (e.g., observed measurements) of the physical electrodes $33_1$-$33_4$ within the patient body (e.g., patient reference frame) to an applied potential field to determine responses (e.g., locations) of the electrodes, as represented the dashed circles. If utilized, the magnetic-based medical positioning system measures the response (e.g., location) $28_2$ of the magnetic sensor in the patient body, as represented by the dashed vector $29_2$. As shown by the magnified portion of FIG. 5C, measured responses of the physical electrode(s) (e.g., $35_1$) and/or sensor(s) (not shown) and the predicted responses of the electrode (e.g., $31_1$) and or sensors (not shown) each contain some unknown error or noise (e.g., uncertainty). However, in an embodiment, the uncertainty of the measured responses and predicted responses may partially overlap. The predicted measurements and the observed measurements are then utilized to predict true (e.g., updated) or calculated locations of the electrodes $37_1$-$37_4$ as represented by the X's in FIG. 5C. As shown in the magnified portion of FIG. 5C, the calculated location $37_1$ may reside in the overlap of the predicted response location and the measured response location. In any embodiment, the calculated locations typically have a higher accuracy than locations resulting from either the predicted responses or the observed responses. The calculated locations may then be output to a display. See, e.g., FIG. 1. That is, an updated representation or rendering of a catheter or other medical device may be output to the display using the calculated locations.

Catheter Model

The following provides one simplified catheter model that allows identifying locations of magnetic sensors and electrodes within a catheter reference frame. The following model is directed to a rigid catheter with a single magnetic sensor and four electrodes having a known orientation relative to the magnetic sensor. However, it will be appreciated that other more complex catheter models are possible and considered within the scope of the present disclosure. In some embodiments, the catheter model may provide for catheter deformations such that the model includes deformable sections (e.g., a small number of curvature and torsions along a Frenet-Serret reference frame) for use with a rigid-body transformation (e.g., a unit quaternion and translation) to describe the catheter shape, and/or position and orientation in the patient reference frame. In an example, catheter models for use in determining electrode locations in a catheter reference frame are described in U.S. Provisional Application No. 62/756,915, titled "Mechanical Models of Catheters for Sensor Fusion Algorithms", filed on Nov. 7, 2018, the entire contents of which is incorporated herein by reference.

Figure 6:
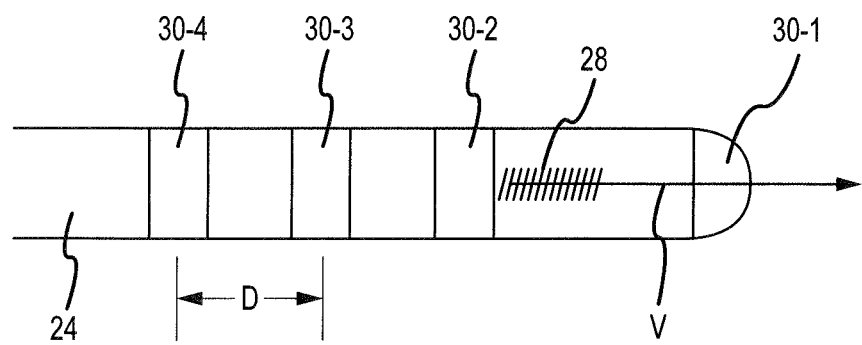
FIG. 6 illustrates a catheter having a magnetic sensor and multiple electrodes.

FIG. 6 depicts a side view of a medical device or catheter 24 with a single magnetic position sensor 28 and four electrodes 30-1, 30-2, 30-3, 30-4 (hereafter 30 unless specifically referenced). In order to reduce the complexity or reduce the dimensionality of the model (e.g., number of model parameters), it may be desirable to determine the position and orientation of the electrodes in the catheter reference frame as a function of the position of the magnetic sensor. For example, using specifications associated with the catheter (e.g., manufacturer specifications detailing the position of the electrodes 30 with respect to the magnetic position sensors 28), the locations of the electrodes in the catheter reference frame may be determined from the position of the magnetic sensor(s). For example, based on a position and orientation of a magnetic position sensor 28 (e.g., a five or six degree-of freedom sensor), a vector for the magnetic position sensor can be determined. In some embodiments, the vector can be in a direction facing towards the distal end of the magnetic position sensor 28 (e.g., magnetic coil) and can be coaxial with the magnetic position sensor 28. Because the magnetic position sensor 28 is disposed within a shaft of a rigid catheter, the position and orientation of the catheter shaft can be determined based on the vector associated with the magnetic position sensor. Specifications associated with a positioning of one or more electrodes 30 on the shaft with respect to the magnetic position sensor 28 (e.g., manufacturer specifications) can be used to determine model positions of the electrodes 30 in the catheter reference frame (i.e., along the vector). Accordingly, a model equation (e.g., state vector) may be determined that identifies the location of the sensor 28 and electrodes 30 in the catheter reference frame. That is, coupled with sensor location and electrode spacing, all electrode and sensor positions and orientations are known in the catheter reference frame.

Catheter Position and Orientation Model

The state vector for the above described catheter model has six degrees-of-freedom. Three degrees-of-freedom for position (i.e., x, y, z) which may define an origin of the catheter reference frame and three degrees of freedom for orientation (i.e., yaw, pitch, roll); a 3D bivector ($b_{yz}$, $b_{zx}$ and $b_{xy}$), which is the log of the quaternion. The catheter shape model may be transformed into the patient reference frame utilizing any transformation (e.g., catheter transformation) that preserves shape and size of the catheter model. That is, catheter position and orientation model may be represented by a rigid-body transformation (e.g. six degree of freedom rigid-body transformation) that translates the state vector of the shape model into the patent reference frame. For instance, such a transformation may align the origin and orientation of the catheter model (e.g., vector in an embodiment) relative to the origin of the patient reference frame (e.g., as determined by the patient reference sensor). At such time, model locations of the magnetic sensor and electrodes are estimated within the patient reference frame. Of note, the origin of the patient reference frame as well as the origin of the catheter reference frame may shift due to patient motions (e.g., respiration, physical patient movement, etc.). Accordingly, the transformation and registration between the patent reference frame and the catheter reference frame may be updated.

Magnetic Model

The following provides one magnetic model that transforms from patient relative coordinates (e.g., patient reference frame) to the magnetic-based coordinate system. That is, the magnetic model takes a location in the patient reference frame having an origin defined by the PRS and generates a location in the magnetic reference frame. In an embodiment, the magnetic model is a rigid transformation from the patient coordinate frame/patient reference frame 6 to the magnetic-based coordinate system 4. As noted, the origin of magnetic based coordinate system is based on the magnetic-field generator while the origin of the patient reference frame is defined by the patient reference sensor. In an embodiment, the origin of the patient reference frame may be offset from the patient reference sensor. In such an embodiment, a coordinate may be mapped through the following relationships as if they were 4×4 matrices in homogenous coordinate systems:

$pat_k = PRSToPat_k ref_k$ $mag_k = PatToMag_k pat_k$ where $ref_k$ is the value of a coordinate in a patient body at time k, $pat_k$ is the value of the coordinate aligned with the patient reference frame at time k, and $mag_k$ is the value of the coordinate in magnetic-based coordinate system 4 at time k. The PRSToPat transformation rotates the coordinate to align it with the patient frame of reference while the PatToMag transformation rotates the patient frame of reference to the magnetic frame of reference. In an embodiment, these relations may be used to generate a magnetic value for a location in the patient reference frame. It will be appreciated that additional magnetic models are possible and considered within the scope of the present disclosure. In an example, a magnetic model for use in transforming between patient relative coordinates to magnetic coordinates is described in U.S. Provisional Application No. 62/756,936, titled "Patient Reference Sensor Model for Medical Device Localization based on Magnetic and Impedance Sensor Measurements", filed on Nov. 7, 2018, the entire contents of which is incorporated herein by reference.

The magnetic model may form a part of the overall or composite system model. During implementation, the model is queried to predict sensor locations in the patient reference frame. Subsequently, these predictions are utilized with sensor locations measurements to further refine the estimated locations of the sensors in the patient reference frame.

Impedance Model

Within the context of a sensor fusion process, the usefulness of impedance measurements to locate physical catheters and their electrodes in a three-dimensional space (e.g., patient reference frame) depends on having an effective model, for any catheter configuration, to predict the impedance measurements within an electrical or impedance potential field. That is, based on a predicted location (e.g., model location) of a catheter and/or catheter electrodes (e.g., model electrodes) in a patient reference frame (e.g., three-dimensional space), it is desirable to predict the impedance measurements of the modeled catheter electrodes to refine the location of the physical catheter and/or its electrodes and/or to update the impedance model. It has been further recognized that previous efforts of impedance modeling of electrodes locations has, in some instances, lacked accuracy due to the failure to account for noise.

In an embodiment, an impedance model transforms between the patient coordinate system and the impedance measurements (e.g., PatToImp). Further, the impedance model may incorporate noise and and/or distance dependent modeling errors between individual electrodes to improve the estimation of impedance measurements for determining electrode locations within a patient. In an embodiment, the impedance model is a stochastic process where a true state of the model is a hidden or latent state that is determined. The model generates estimates of electrode impedance measurements in a three-dimensional space (e.g., location-to-impedance-values). Such estimates and/or the model may be refined based on actual impedance measurements of electrodes located in the three-dimensional space. In an embodiment, such an impedance model implements various separate methodologies, which can be used in combination.

In an embodiment, a first methodology is directed to modeling the location-to-impedance-value as mapping a linear combination of harmonic basis functions, such as regular solid harmonics. However, it will be appreciated that additional harmonic basis functions are possible and considered within the scope of the present disclosure. However, it is believed that regular solid harmonic basis functions provide suitable descriptiveness with reduced degrees of freedom, simplifying the model. Further, as the electrodes are located within a common blood pool, they experience generally uniform conditions such that a Laplacian of the harmonic basis functions should be zero providing a constraint for the model. Yet further, the linear combination of harmonic basis functions may be constrained to obey Kirchhoff's voltage law. Collectively, this helps to account for spatial nonlinearity of the impedance measurements. In an embodiment, a second methodology is directed to modeling the measurement noise characteristics of the impedance system, including covariance among measurements from distinct electrodes. In an embodiment, a third methodology is directed to introducing an artificial measurement noise covariance among distinct electrodes that falls off with the distance between those electrodes. This noise term represents the amount of otherwise un-modeled error and helps to account for spatial nonlinearity of the impedance measurements and/or respiration-related artifacts.

The hardware for impedance-based location measurements include of a set of electrical patches affixed to the patient/patient reference frame (e.g. 6 patches: neck, leg, chest, back, right, left). See. FIGS. 3A-3D and 7A. AC voltages are applied to sets of patch pairs (e.g. back→left, left→chest, right→back, chest→right, neck→back, leg→back) and the potentials (e.g., impedances) on each catheter electrode 30 of a catheter 24 disposed in the resulting impedance field are measured while each patch pair is driven. See FIG. 7A. The measured potentials depend on the relative impedances between the electrode(s) and each of the driven patches. That is, each driven patch pair induces a potential field across the patient refence space that the electrodes measure. Accordingly, the intent of the impedance model is to model the potential field and its measurement characteristics such that an impedance measurement may be estimated for any location within the potential field. By way of example, after establishing such and impedance model of a three-dimensional space (e.g. patient refence space), impedance values may be estimated or predicted for any location in that space at a given time.

Figure 7A:
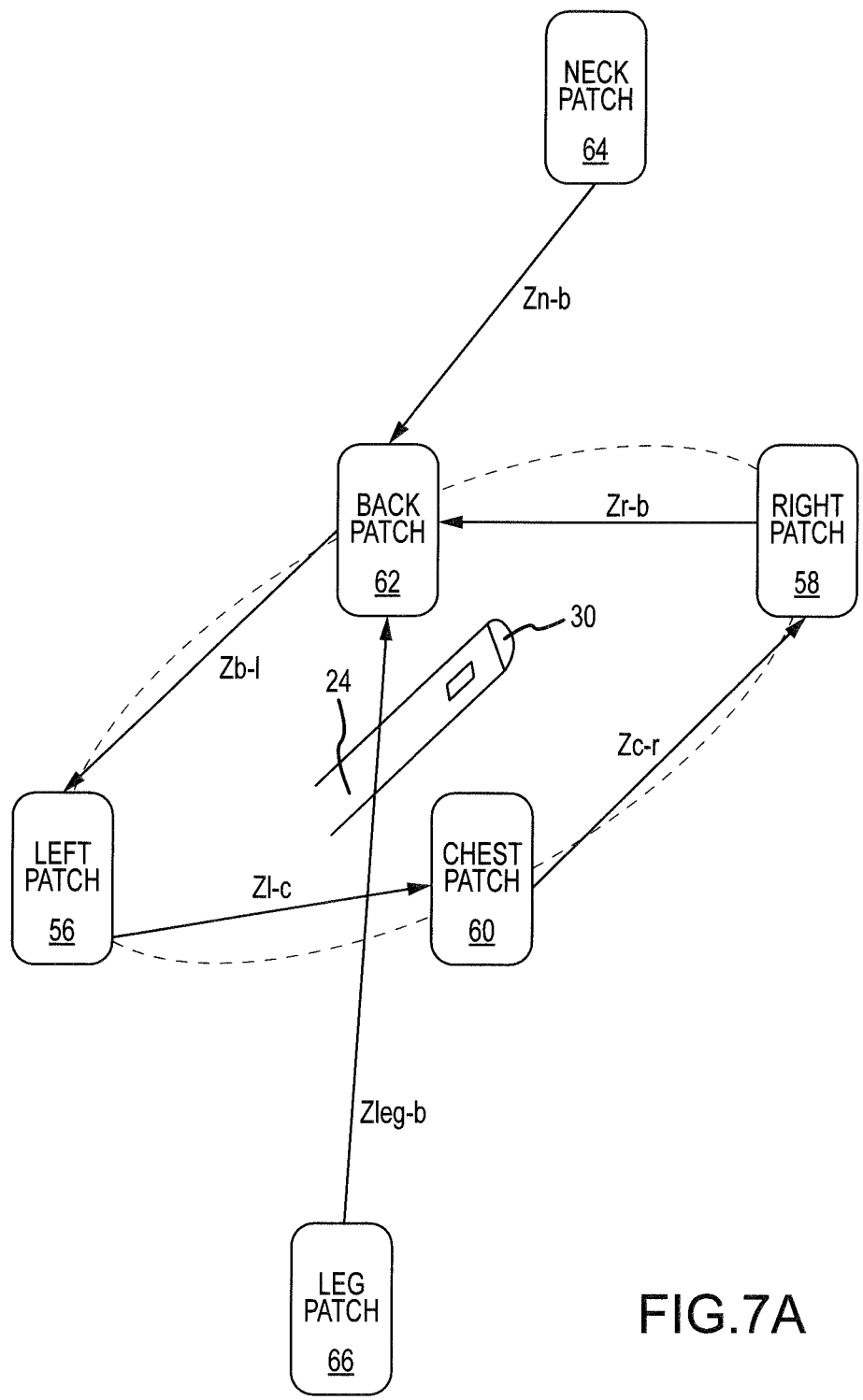
FIG. 7A illustrates a mathematical graph of patch electrodes.
Figure 8:
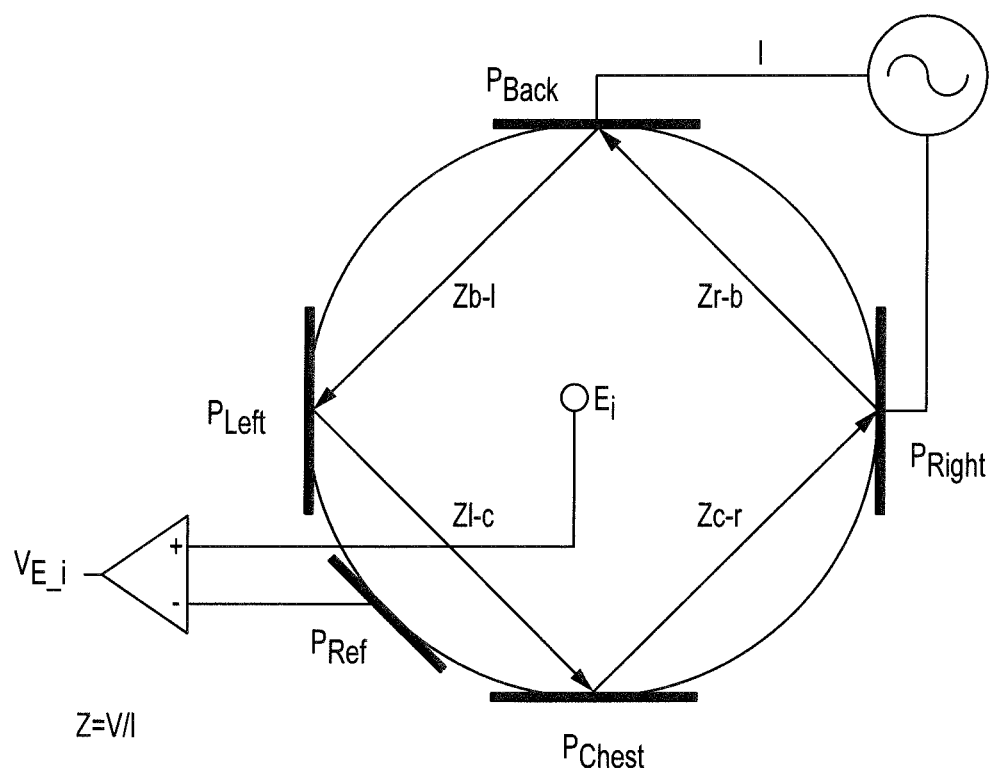
FIG. 8 illustrates a constraint defined by a set of external impedance patch pairs.

FIG. 7A illustrates a mathematical graph of the impedance patches where each patch forms a vertex of the graph and a graph edge (e.g., solid connecting line) extends between the vertexes of each driven patch pair. In a mathematical graph, a cycle is a path of edges and vertices wherein a vertex is reachable from itself. That is, the cycle forms a closed loop. In the present embodiment, the set of driven patch pairs defines a single cycle: back→left→chest→right→back. Each cycle of the graph (i.e., one in the present embodiment) that forms a closed loop or circuit (e.g., cycle) is constrained by Kirchhoff's voltage law, which implies that the potential differences around that cycle must sum to zero. That is, $Z_{B-L}+Z_{L-C}+Z_{C-R} Z_{R-B}=0$. See FIG. 8. Correspondingly, the sum of driven potentials on any electrode from that cycle must be zero as the potential drop around the circuit back→electrode→left→electrode→chest→electrode→right→electrode→back must also be zero.

Based on these constraints, the number of independent impedance potential fields is the number of driven patch pairs (i.e., six in the present embodiment) less the number of cycles (i.e., one in the present embodiment) in the graph. In the present embodiment, there are five independent impedance potential fields. Further, there is a linear mapping from these independent impedance potential fields to the larger set of potentials driven by the patch pairs. For the set of driven patch pairs shown in the present embodiment, the mapping is as follows:

$$\begin{bmatrix} z_{back \to left} \\ z_{left \to chest} \\ z_{right \to back} \\ z_{chest \to right} \\ z_{neck \to back} \\ z_{leg \to back} \end{bmatrix} = .5 \begin{bmatrix} -1 & 1 & 0 & -1 & 0 \\ 1 & 1 & 0 & 1 & 0 \\ -1 & -1 & 0 & 1 & 0 \\ 0 & 0 & 1 & 0 & 1 \\ 0 & 0 & -1 & 0 & 1 \end{bmatrix} \begin{bmatrix} y_{left \to right} \\ y_{back \to chest} \\ y_{neck \to leg} \\ y_{xy} \\ y_z \end{bmatrix}$$

Where z is the vector of measured or estimated potentials, and y is the vector of the independent impedance potentials, which, in an embodiment, are hidden state variables of a stochastic process. The numeric matrix, denoted M below, maps the five independent impedance potential fields y to the six potentials z. In an embodiment, the matrix M forms an observational model for the stochastic process. The independent impedance potential fields represent virtual potential fields that, in the presented embodiment, are never excited though exist within the system. That is, the independent impedance potential fields exist between the non-exited patch pairs. Two of these independent impedance potential fields $y_{left-right}$ and $y_{back-chest}$ are shown in the graph of FIG. 7A. By way of example, $y_{left-right}=z_{left-chest}+z_{chest-right}$ and $-y_{left-right}=z_{right-back}+z_{back-left}$. The independent impedance potential field for $y_{xy}$ is illustrated in FIG. 7B. This potential field is based on the four patches, back, left, chest right that lie in a substantially common plane XY as illustrated in FIG. 7A. A similar graph may be provided for the YZ plane of the patient to describe the remaining independent impedance potential fields. Thus, the independent impedance potential fields may be calculated or estimated as algebraic functions of the measured impedance values. In an embodiment, the independent impedance potential fields define state variables of the stochastic process and are described with harmonic basis functions as set forth below.

Each time point and for each independent driven patch pair or 'impedance mod', model impedance measurements for each independent impedance potential field i and electrode j are set forth as follows:

$$y_{ij}=\varphi_{ij}+\varepsilon_{ij}$$

and:

$$z_k=\text{Vec}(My_j)+v_k$$

Where $\varphi_{ij}$ is a potential in independent impedance potential field i for electrode j computed from a series of harmonic bases $Y_l$, $\varepsilon_{ij}$ is a modeling error term which covaries between a pair of electrodes as function of their distance, and $v_k$ is a measurement noise term.

For each independent driven patch pair or impedance mod i', $\varphi_{i',j}$ is a function of the electrode location $x_j$ (e.g., in the patient reference frame) and of the state variables of the impedance model (e.g., Patient to Impedance transformation). In an embodiment, the impedance transformation may be a global dynamic non-rigid transformation that maps the patient frame of reference to the impedance frame of reference. $\varepsilon_{i'}$ is the vector of all distance dependent modeling error terms for impedance mod i' and is modeled as a multivariate normal random variable whose entries have a covariance dependent on the distances between pairs of electrodes. Finally, v, the vector of the electrical noise terms for all electrodes, is a multivariate normal random variable reflecting electrical noise characteristics of the measurement system. This model of impedance measurement behavior is used as part of the sensor fusion process or algorithm, such as a recursive Bayesian estimator (e.g. an extended Kalman filter or particle filter), to fit impedance and catheter state variables to impedance measurements and other measurements.

In an embodiment, $\varphi_{ij}$ is a linear combination of basis functions. Each basis function at a point in space maps to an electrical value of the modeled potential field to an electrical value (e.g, voltage, impedance, etc.). If electrodes are at locations $x_j$ then:

$$\varphi_{ij} = \sum_\ell b_{i,\ell} Y_\ell(x_j)$$

Where $Y_l$ is a scalar-valued function evaluating the l'th solid harmonic basis function for an electrode location, and $b_{i,l}$ is the weights on the basis functions (e.g., l'th basis function) relating the patient frame of reference to the impedance potential field. All basis functions $Y_l$ should be harmonic. That is, the Laplacian everywhere should be zero. In an embodiment, $Y_l$ can be the regular solid harmonics of up to a predetermined order. For example, $Y_l$ can be the regular solid harmonics of up to the fourth order. Use of harmonics up to the fourth order results in 25 basis functions per electrode. As will be appreciated, limiting the harmonic basis functions to the fourth order truncates information in higher order harmonics, which may provide additional description of the potential field. The exclusion of this information is accounted for in the modeling error term ε. In an embodiment, the weights $b_{i,l}$ may be set to predetermined or default values, which may be based on experimentally determined baselines. During operation of the impedance model, these weights $b_{i,l}$ are adjusted to fit impedance and catheter state variables to impedance measurements and other measurements.

Distribution of the modeling error term ε:

The intent of the modeling error term is to represent sources of unmodeled signals in the impedance measurements, such as unmodeled high-order terms of the harmonic basis or perturbations caused by patient respiration. Explicitly incorporating the expected magnitude of unmodeled phenomena or error in the impedance basis model makes the system robust to such discrepancies.

For each independent impedance mod i', let $\varepsilon_j = n_j + r_j$ where $n_j$ is a multivariate normal random variable representing error due to nonlinearity of the impedance not modeled by the $g_k$ and $r_j$ is a multivariate normal random variable representing error due to, for example, unmodeled respiratory artifacts.

In an embodiment $n_j$:

$$n_j = N\left(0, \begin{bmatrix} h(|x_l - x_l|) & \ldots & h(|x_l - x_m|) \\ \ldots & \ldots & \ldots \\ h(|x_m - x_l|) & \ldots & h(|x_m - x_m|) \end{bmatrix}\right) \text{ where}$$

$$h(d) = ae^{-bd^2}$$

Where N is a normal random distribution, 0 represents the mean of the distribution and the matrix h represents the covariance for each electrode based on the absolute distance d (e.g., vector) between each electrode (i.e., $|x_\#-x_\#|$). See. e.g., FIG. 6. This choice of covariance results in error expected to vary smoothly over space. The parameter a represents a magnitude of the modelling error. The larger the parameter a, the greater the expected magnitude of nonlinearity-derived error. The parameter b represents a width or radius over which the modelling error decays. The larger the parameter b, the smaller its expected distance scale.

In an embodiment, $r_j$:

$$r_j = N\left(0, \begin{bmatrix} c & \ldots & c \\ \ldots & \ldots & \ldots \\ c & \ldots & c \end{bmatrix}\right)$$

At each time i, respiration applies a shared translation to all points of each independent impedance potential field. The parameter c controls the magnitude of respiratory error. In an example, a system and method for modeling a respiratory error or artifact is described in U.S. Provisional Application No. 62/756,926, titled "Respiration Model for Device Localization Based on Impedance Sensor Measurements", filed on Nov. 7, 2018, the entire contents of which is incorporated herein by reference.

Distribution of the electrical noise term $v_k$:

For each driven patch pair j:

$$v_k = \sim N\left(0, \begin{bmatrix} d+e & \ldots & d \\ \ldots & \ldots & \ldots \\ d & \ldots & d+e \end{bmatrix}\right)$$

In this embodiment, each electrode has a noise component of variance e that is independent of other electrodes and a noise component of variance d that is shared with other electrodes.

In use, the impedance model mathematically defines the impedance field for a patient reference frame. In an embodiment, the impedance field is defined such that impedance potentials for a set of driven patch electrodes, at any location in the impedance field, are a function of a set independent impedance potential fields, which are mapped to the impedance potentials. Various method may be implanted to generate the impedance model. In an embodiment, the impedance model is generated on the fly during a procedure. That is, a catheter 24 may be disposed within an impedance field at the beginning of a medical procedure. See FIG. 7A. During the procedure, electrode impedances measurements are acquired as the catheter 24 moves through the impedance field and the independent impedance potential fields are mapped to the impedance measurements. In another embodiment, an initial impedance model may be generated using a mapping catheter having a high number of electrodes. In such an embodiment, the mapping catheter may be moved (e.g., swept) around an internal patient cavity (e.g., heart chamber) to acquire impedance measurements for a large number of locations. This may result in an impedance model having a large number of locations and corresponding impedance measurements and mapped independent impedance potential fields. In such an embodiment, the mapping catheter may be removed after generating an initial impedance model and replaced with a catheter used to perform a medical procedure (e.g., an ablation catheter). On exemplary mapping catheter is described in U.S. Pat. No. 8,744,599, entitled "High Density Mapping Catheter", which is hereby incorporated by reference in its entirety. In a further embodiment, a default impedance map may be provided that assumes an initial state of the impedance model. In this embodiment, subsequent impedance measurements are used to more rapidly update the model for a current impedance field or patient reference space. In any embodiment, locations, impedances and independent impedance potential fields may be recorded. Subsequently, the impedance model may utilize this information to, for example, interpolate impedance measurements for locations between known locations in the modeled impedance field.

In an embodiment, the independent impedance potential fields and their parameters are state variables of a stochastic process such that they may evolve over time. Initially the impedance model estimates a set of impedance measurements $z_{i,est}$ (e.g. back→left, left→chest, right→back, chest→right, neck→back, leg→back) for electrodes j at a locations $x_j$. See. e.g., predicted electrode locations $30_1$-$30_4$ in the heart 52 in FIG. 5B and predicted measurements $31_1$-$31_4$ in FIG. 5C. In an embodiment, the predicted locations for these electrodes may be estimated in the patient reference frame using a catheter model. The predicted set of impedance measurements are generated, in an embodiment, based at least in part on the weights $b_{i,j}$ applied to the harmonic basis functions. When implementing the impedance model, a set of impedance measurements (e.g., actual measurements) $z_{i,act}$ may be obtained for a corresponding physical electrode in the patient reference frame. See. e.g., measurements $35_1$-$35_4$ in FIG. 5C. The predicted measurements $z_{i,est}$ may be utilized with the actual measurements $z_{i,act}$ (e.g., observable parameters/electrode impedance measurements, calculated independent impedance fields) to determine, for example, a correction or gain in a stochastic process. This correction/gain may then be utilized to adjust hidden state variable of the impedance model. For example, the weights $b_{i,j}$ as well as other hidden state variables (e.g., basis functions of the independent impedance potential fields) of the impedance model may be adjusted to better fit or match the actual impedance measurements. In application, the impedance model adjusts (e.g., recursively) to more closely approximate the actual impedance measurements. Accordingly, the updated impedance model may subsequently be used to predict an impedance measurement for locations (e.g., as predicted by a catheter model) in the modeled potential field. Further, the correction/gain may be utilized to estimate an updated electrode location in the patient reference frame. See, e.g., true locations $37_1$-$37_4$ in FIG. 5C.

In an embodiment, an Extended Kalman filter is used to infer hidden state variables corresponding to the hidden state variables of the model. From the hidden state variables, at any time, hidden state measurements (e.g., impedance values at locations in space) can be predicted and estimates of the state variables can be updated using an Extended Kalman filter framework in a fashion that allows updates to those parts of the hidden state variables that are accessible. Thus, at any instant in time, while there may not be enough information to determine parts of state variables, by using the Extended Kalman filter framework, predictions associated with appropriate parts of the state variables associated with the transformation from the location in the patient reference frame to impedance measurement can be made.

Differences between the predictions for the appropriate parts of the state variables associated with the model and actual measurements can be made and the appropriate parts of the state variables can be updated based on the differences between the predictions and the actual measurements. As such, the state variables can be modified over a given period of time, rather than at a given instant in time. For example, the prior prediction of the appropriate parts of the state variables can be corrected based on measurements at a current time point.

As discussed further herein, the impedance model forms a part of the overall or composite system model. During implementation, the impedance model is queried for use with predicted electrode locations in the patient reference frame as estimated by the catheter model. More specifically, the impedance model is used to predict measurements for each electrode location in the patient reference frame. Subsequently, these predictions are utilized with actual electrode measurements to further refine the estimated locations of the electrodes in the patient reference frame as well as update the impedance model.

Figure 9:
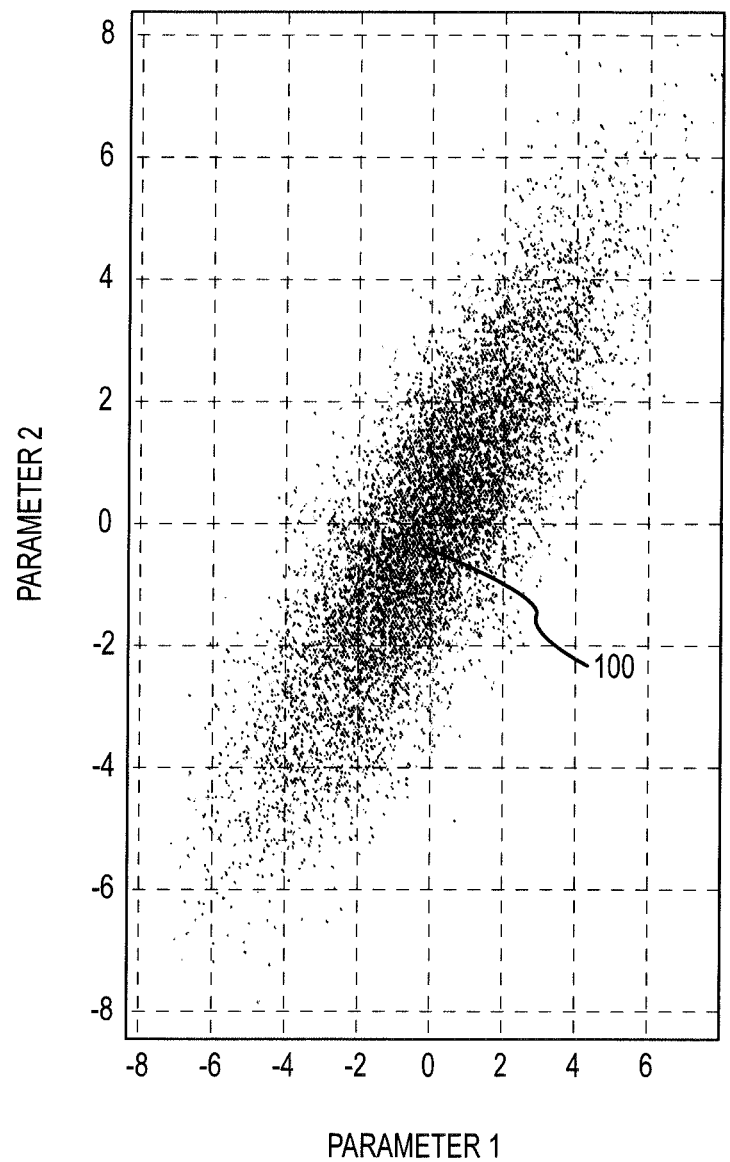
FIG. 9 illustrates a state distribution.

Collectively, the models fully describe the movement of the medical device. Stated otherwise, the models describe possible states of a stochastic process and represent individual state variables of the system. Generally, knowledge of the state variables at an initial time with at least partial knowledge of system inputs and/or outputs permits estimating current states and/or subsequent states of the system as points or a distribution in a state space. The state of the system can be represented as a distribution 100 of possible states within the state space (i.e., represented as points in the state space). See, e.g., FIG. 9.

The overall system is a stochastic process as are a number of the system components (e.g., individual models). To provide improved modeling and estimation of the system, noise should be included within the system model. The observational model utilizes new measurements (e.g., with some amount of noise) with the previous state of the system to estimate or predict a new state of the system. In an embodiment, the process fuses impedance measurements from electrodes of a physical catheter with predicted electrode measurements based on a catheter model to update the predicted shape of a medical device or catheter disposed within a patient reference frame as well as update the various variables of the various models. For instance, the disclosed system may predict and update states of the system approximately 100 times per second. From the perspective of a user, such updates (e.g., which may be output to a display) appear continuous.

The overall stochastic process estimates new locations of the medical device and/or new locations of the electrodes of the medical device as well as new variables of the various models. In an embodiment, the process assumes that the state of a system at time k evolved from a prior state at k−1 according to the equation:

$$x_k = F_k(x_{k-1}) + w_k$$

where:

$x_k$ is the state vector containing parameters of interest for the system (e.g., parameters of the models). This equation is used to predict subsequent states with error.

$F_k$ is the state transition matrix which applies the effect of each system state parameter at time k−1 to the system state at time k.

$w_k$ is the vector containing process noise terms for each parameter (e.g., model) in the state vector.

Measurements of the system, with error, are also performed at each time step according to the model:

$$z_k = h_k(x_k) + v_k$$

where:

$z_k$ is the measurement vector; the set of variables measured by the sensors (e.g., impedance measurements, magnetic sensor measurements, etc.).

$h_k$ is the observational model (i.e., transformation matrix) that maps the state vector parameters into the measurement domain. Stated otherwise, the observational model defines the relationship between the true state vector and noisy measurements; and $v_k$ is the vector containing the measurement noise terms for each measured variable in the measurement vector.

The stochastic process is utilized to determine a true state of the system and or system models, which are hidden or latent states. The purpose of the process it to generate estimates of the system state (e.g., electrode locations, hidden variables of the models) and determine the true state from these estimates. In an embodiment, an estimator is implemented in an extended Kalman filter adapted for use with non-linear system models or linearized system models and/or with models having non-Guassian noise distributions. However, it will be appreciated that variations may be implemented using other estimators such as the unscented Kalman filter, Markov Models and/or particle filters, which each may be applied to nonlinear systems and/or systems with non-Gaussian noise distributions.

Each estimate of the estimator is a mean (i.e., center of a distribution of state estimates) and covariance describing a probability about the mean. In application, the estimates include an a priori estimate (predict) prior to incorporating the measurements and an a posteriori estimate (update) after incorporating the measurements. The a priori estimate uses the state estimate from the previous time step to produce an estimate (e.g., prediction) of the latent state (mean $\underline{x}_{k|k-1}$ and covariance $\underline{P}_{k|k-1}$) at the current time step:

$$\underline{x}_{k|k-1} = F_k \underline{x}_{k|k-1}$$

$$\underline{P}_{k|k-1} = F_k \underline{P}_{k|k-1} F_k^T + Q_k$$

That is, the a priori estimate is an estimate from the transformation matrix that produces an estimated distribution and covariance from the prior state (i.e., k−1). The transformation matrix takes every point in the original distribution and moves it to a new predicted distribution, which may have an expanded covariance (e.g., the addition of $Q_k$ to the covariance matrix P) to account for unknown system noise. In the a posteriori estimate, the current a priori prediction is combined with the observation model to refine the state estimate. More specifically, the observational model maps the estimation (e.g. mean $\underline{x}_{k|k-1}$ and covariance $\underline{P}_{k|k-1}$) to the measurement domain to predict measurements:

$$\underline{z}_k = h_k \underline{x}_{k|k-1}$$

The covariance of predicted measurements $\underline{z}_k$ may be compared with the covariance actual measurements $z_k$ of observable parameters (e.g., electrode measurements and sensors measurements of the system):

$$y_k = z_k - \underline{z}_k$$

Figure 10:
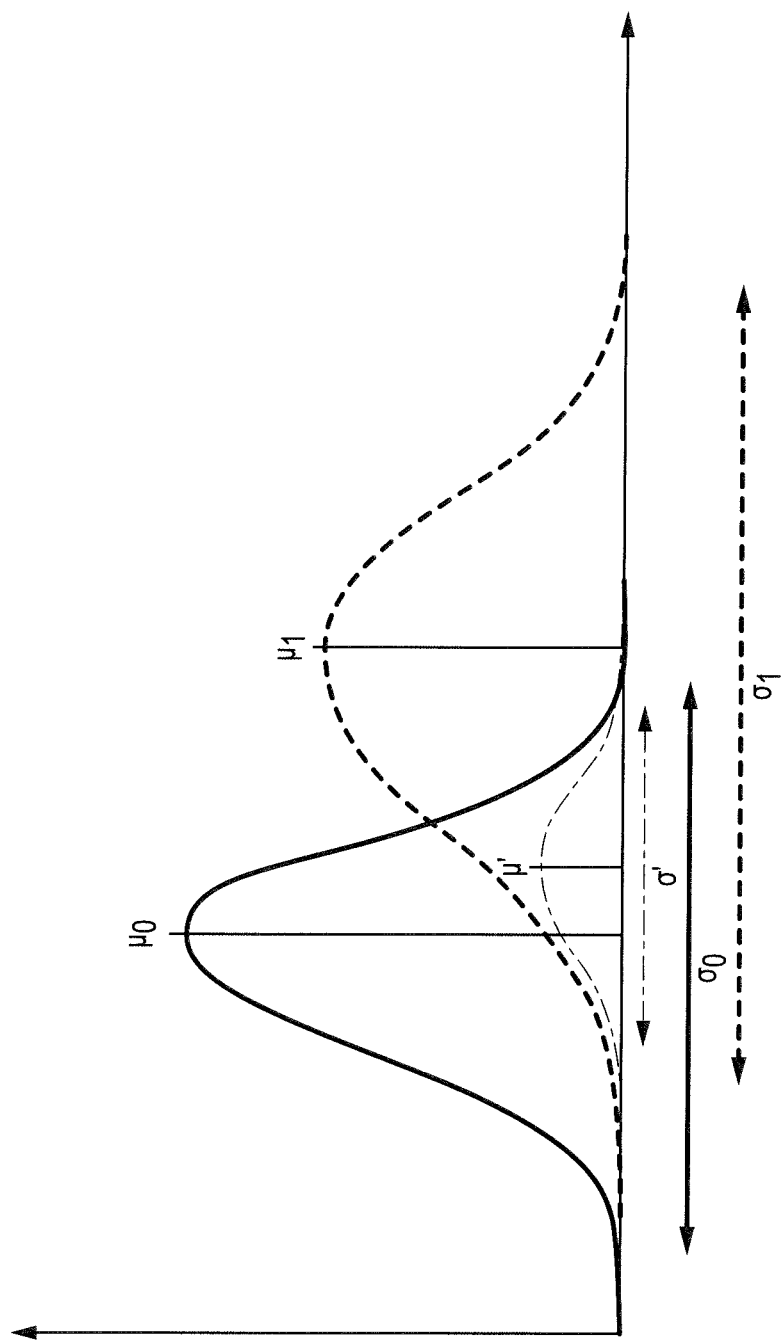
FIG. 10 illustrates one dimensional comparisons of observed states and measured states.

This allows for determining the gain K of the system, where K minimizes the expected sum squared error between $\underline{x}_{k|k}$ − $x_k$. This is graphically illustrated in FIG. 10 which is a 1-D representation of the state distribution combined with the observational model that produces the predicted measurements with a first predicted mean to and a first predicted covariance Go. The actual observation measurement is represented by a second distribution with a second mean $\mu_1$ and a second covariance $\sigma_1$. The overlap of these distribution defines the system gain (e.g., Kalman gain), which is used to correct the estimated state and estimated covariance. Stated otherwise, the two distributions are fused to generate an updated distribution with a fused mean $\mu'$ and a fused covariance $\sigma'$ (e.g., two Gaussian distributions multiple together generate an Gaussian distribution of the overlapping portion of these two distributions). The gain K may be combined with the estimated state distribution and estimated covariance to generate an updated state distribution (e.g., updated state mean and updated covariance):

$$\underline{x}_{k|k} = \underline{x}_{k|k-1} + K_k y_k$$

$$\underline{P}_{k|k} = (I - K_k H_k) \underline{P}_{k|k-1} (I - K_k H_k)^T + K_k R_k K^T.$$

The updated mean state may be utilized to determine updated or true locations (e.g., calculated locations) of the electrodes and/or magnetic sensors. Further, this state may be utilized to update the various state variables of the various models. In an example, multiple models for use in determining electrode and or sensor locations in three-dimensional space (e.g., a patient reference frame) are described in U.S. Provisional Application No. 62/756,941, titled "Method for Medical Device Localization Based on Magnetic and Impedance Sensors", filed on Nov. 7, 2018, the entire contents of which is incorporated herein by reference.

Constraints

While the above noted process allows for predicting a current state of the system, it is further realized that the state vector and corresponding estimates of the state may be subject to various constraints. Such constraints may be utilized to limit or otherwise refine the state distributions and thereby improve the overall accuracy of the system. Given a state vector, x, a model constraint can be expressed in a functional form as g(x)=0. In this form, any true state must satisfy this equation. By way of example, impedance measurements are made by driving current across surface patch electrodes to excite an electrode. As previously noted, the electrode excitation process occurs rapidly and sequentially as different sets of patch electrodes are selected and one or more of the unexcited (in an embodiment) surface electrodes are used to measure voltages. During the delivery of the excitation signal (e.g., current pulse), the remaining (unexcited) patch electrodes may be referenced to the reference or belly patch while the voltages impressed on these remaining electrodes are measured. Potentials across each of the surface patch electrodes may be acquired for all samples except when a particular surface electrode patch pair is driven. In the two dimensional representation shown in FIG. 8, the back, left, chest and right surface patch electrodes define a current loop within the patient body. Kirchhoff's Voltage law dictates a linear constraint on this voltage loop. Specifically, the sum of the driven potentials (i.e., impedances) from that cycle across all of the pairs of patch electrodes must be zero. That is:

$$Z_{B-L} + Z_{L-C} + Z_{C-R} + Z_{R-B} = 0$$

Correspondingly, the sum of driven potentials on any electrode from that cycle must be zero. Accordingly, this constraint may be applied to the portion(s) of the state vector that relates to impedance measurements (e.g., impedance model). Another constraint may be that the magnetic model may be constrained to changes that correspond to a rigid-body transformation without scaling. That is, all identified objects before and after transformation must have the same relative orientations. Other constraints may be applied to the composite model or the independent models. In application one or more such constraints may be applied to limit or otherwise refine the state distributions.

Figure 11:
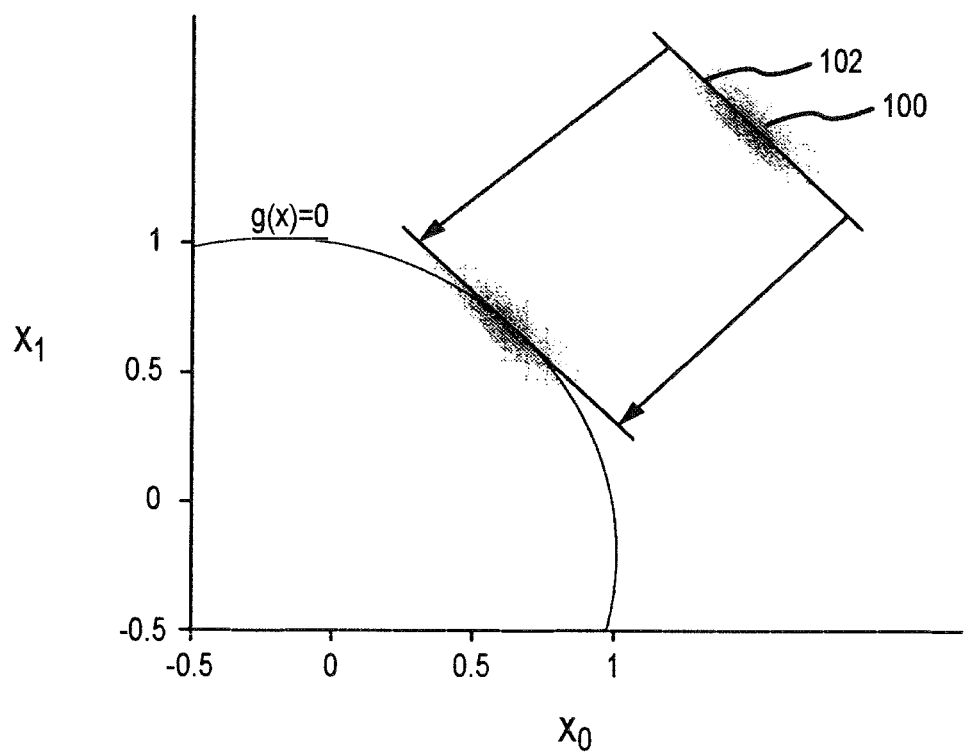
FIG. 11 illustrates a constraint manifold and a state distribution offset from the manifold.

FIG. 11 illustrates a constraint g(x)=0 in relation to a state distribution estimate. As shown, the constraint forms a feasibility manifold or constraint manifold in the state space where the constraint is satisfied. That is, the states where g(x)=0. As shown in FIG. 11 the initial state distribution estimate 100 does not lie on the constraint manifold. Accordingly, to enforce the constraint for the state distribution estimation, the state distribution estimation must be moved to the constraint manifold. This constraint application is performed by generating a delta function that satisfies the constraint and multiplying it by the state distribution estimate to produce a constrained state distribution estimate.

The constraint application may be approximated using a first-order Taylor series expansion which generates a linear representation or tangent line 102 about the mean of the unconstrained state distribution estimate 100. This produces a first-order approximation about the unconstrained mean of the state distribution estimate. This tangent line may be projected to the surface of the constraint. More specifically, this first-order approximation may be projected orthogonally to the null-space of the Jacobian of the constraint:

$$G = \frac{\partial g}{\partial x}\bigg|_{x'}$$

with the distribution projected into the null space of G. With successive projections through G, the estimated state distribution will track the constraint manifold even if the constraint is not exactly linear. The result is that the state distribution estimate is constrained to the constraint.

Figure 12:
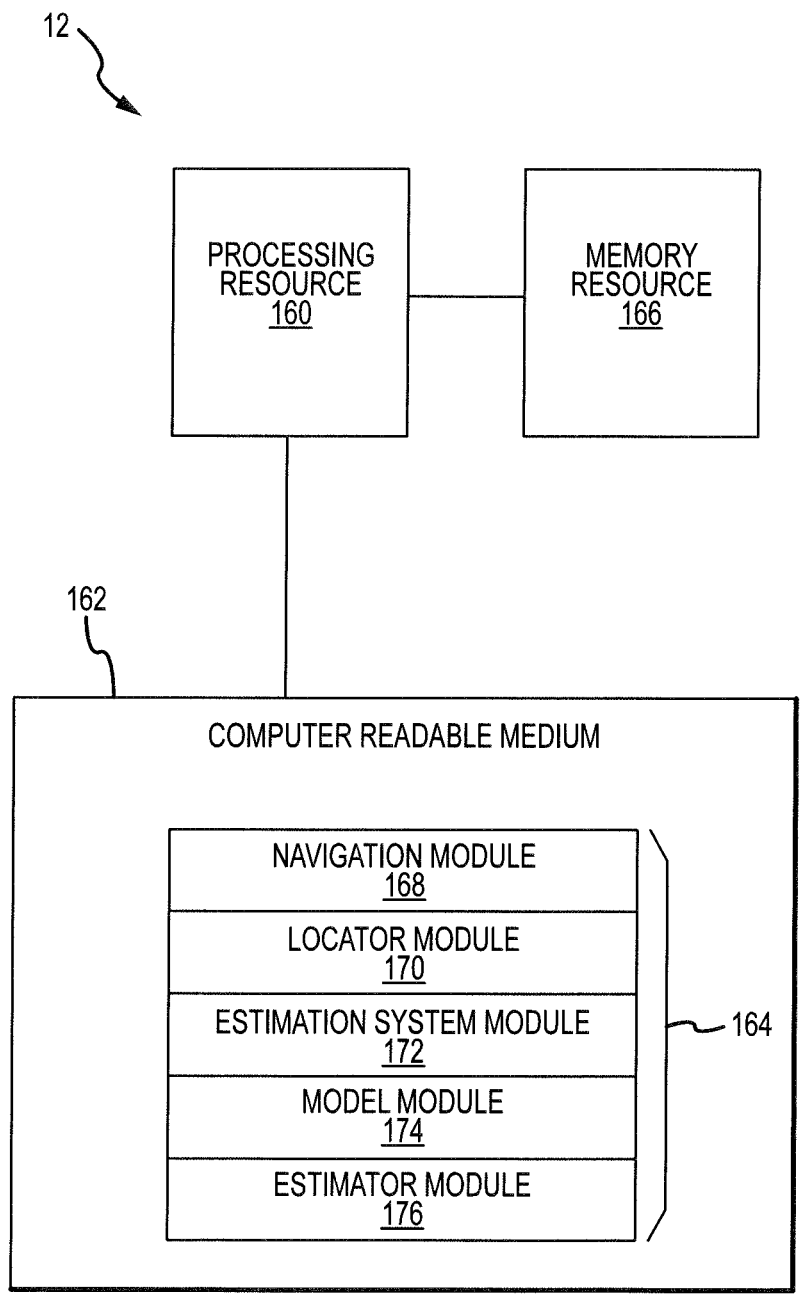
FIG. 12 illustrates a block diagram of an example of a computer-readable medium in communication with processing resources of a computing device, in accordance with embodiments of the present disclosure.

FIG. 12 depicts a block diagram of an example of a computer-readable medium in communication with processing resources of a computing device, in accordance with embodiments of the present disclosure. The main control 12, as discussed in relation to FIG. 1, can utilize software, hardware, firmware, and/or logic to perform a number of functions. The main control 12 can include a number of remote computing devices.

The main control 12 can be a combination of hardware and program instructions configured to perform a number of functions. The hardware, for example, can include one or more processing resources 160, computer readable medium (CRM) 162, etc. The program instructions (e.g., computer-readable instructions (CRI) 164) can include instructions stored on CRM 162 and executable by the processing resource 160 to implement a desired function (e.g., determine an updated location of an electrode on an impedance-based medical device using the observation model, etc.). The CRI 164 can also be stored in remote memory managed by a server and represent an installation package that can be downloaded, installed, and executed. The main control 12 can include memory resources 166, and the processing resources 160 can be coupled to the memory resources 166.

Processing resources 160 can execute CRI 164 that can be stored on an internal or external non-transitory CRM 162. The processing resources 160 can execute CRI 164 to perform various functions, including the functions described above.

A number of modules 168, 170, 172, 174, 176 can be sub-modules or other modules. For example, the estimation module 172 and estimator module 174 can be sub-modules and/or contained within a single module. Furthermore, the number of modules 168, 170, 172, 174, 176 can comprise individual modules separate and distinct from one another.

A navigation module 168 can comprise CRI 164 and can be executed by the processing resource 160 to acquire measurements from a medical device 24 and render an output on a display 16. The measurements can include impedance measurement of an electrode 30 disposed on a catheter and/or impedance surface patch measurements. The measurements can also include magnetic locations of a magnetic position sensor 28 disposed on the catheter and/or magnetic measurements of a patient reference sensor 26. The navigation module 168 may call the location module 170 to obtain updated locations of electrodes and/or sensors of the medical device 24.

A locator module 170 can comprise CRI 164 and can be executed by the processing resource 160 to coordinate the operation of the estimation module 172, the model module 174 and the estimator module 176. In an example, the locator module can receive raw measurements from the navigator module in conjunction with an update request. The locator module 170 may call the estimation system module 172 to pre-process the raw measurements. Once the pre-processed measurements are acquired from the estimation module, the locator module 172 may provide the pre-processed measurements to the estimator 176 to with a request to update the current state of the system.

The estimation system module 172 can comprise CRI 164 and can be executed by the processing resource 160. In an embodiment, the estimation system module 172 defines the stochastic process of the overall system including the state transition(s) and the observational model(s). In an embodiment, the estimation system may be a Kalman system that that implements Kalman filtering techniques. In an embodiment, the estimation system module 172 calls the model module 174 to and estimator module 176 to obtain an updated state estimate.

A model module 174 can comprise CRI 164 and can be executed by the processing resource 160. The model module may include a plurality of individual models. These individual models may include one or more catheter models. In an embodiment, a medical device/catheter may be represented one or more models. Additionally, catheter models may include models of different medical devices for use when more than one catheter is within a patient reference frame. The individual models may also include a magnetic model (e.g., magnetic transformation model) that transforms locations from the patient reference frame of reference to the magnetic reference frame. The individual models may also include an impedance model or impedance transformation model that predicts impedances for locations in the patient reference frame.

An estimator module 176 can comprise CRI 164 and can be executed by the processing resource 160. The estimator module may receive update requests and inputs from the estimation system 172 and provide updated state estimates and/or predicted measurement in response. In an embodiment, the estimator module may be implemented as an extended Kalman filter.

Figure 13:
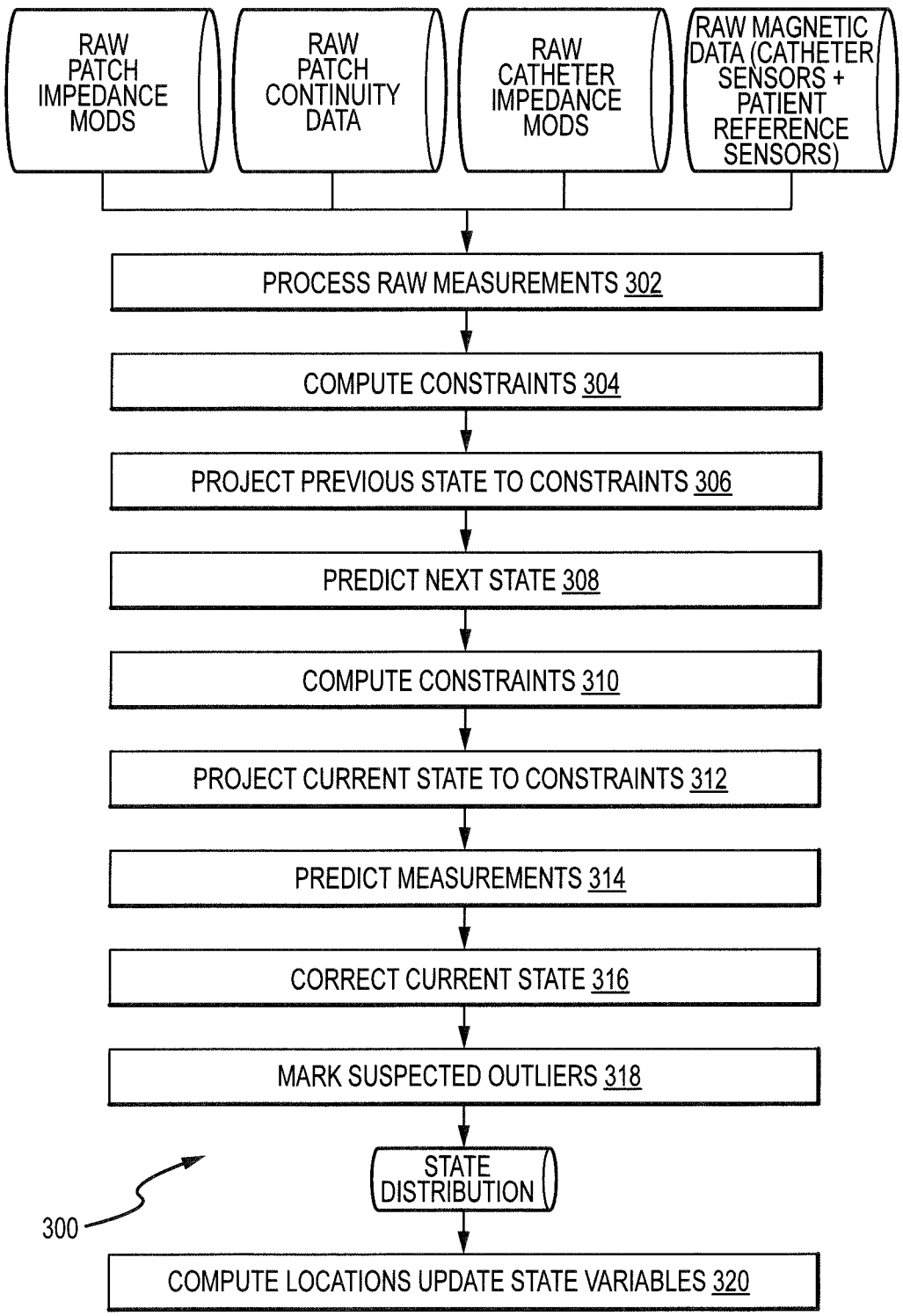
FIG. 13 illustrate a flow diagram associated with determining a latent state of a system to identify electrode locations, in accordance with embodiments of the present disclosure.

FIG. 13 depicts a flow diagram 300 associated with an overall process (e.g., sensor fusion process) to update estimated electrode locations within the three-dimensional space, in accordance with embodiments of the present disclosure. Initially, the flow diagram includes processing raw measurements at box 302. Raw measurements may include raw patch impedance measurements from the surface patch electrodes as well as patch continuity data. The patch continuity data may provide an indication regarding the contact of each surface patch and, hence, reliability of the same. Raw electrode impedance measurements are also received for electrodes of the medical device/catheter (hereafter catheter). Raw magnetic data is also received for magnetic sensors of the catheter and for the patient reference sensor. Processing the raw measurements may include processing to raw measurements to detect any measurements that are outside a predetermined statistical range for the measurements (e.g., have a non-Gaussian error). Any such outlaying measurements may be excluded from subsequent processing At box 304 the flow diagram includes computing one or more state constraints to limit or otherwise refine the state distributions and thereby improve the overall accuracy of the system. Once such constraints are computed, the previous state may be projected to the constraints in box 306. Of note, this may include expanding the covariance matrix for the previous state to account for additional uncertainty or noise in the system for the upcoming prediction. Once this additional process noise is included in the previous state, the previous state may no longer be located on the constraint manifold. Accordingly, the previous state may be moved to the constraint manifold as discussed above.

Once the previous state is projected to the constraint(s), the next state of the system is predicted at box 308 of the flow diagram. That is, a new distribution (e.g., mean and covariance) of the state is generated using the state transition matrix Ft which applies the effect of each system state parameter at time k−1 to the system state at time k. That is, a current state is predicted. Once the new state distribution (e.g., mean and covariance) is generated one or more constraints may be computed for the current state at box 310. The current state may be projected to the constraints at box 312.

Predicted measurements may be generated at box 314 of the flow diagram. That is, the observational model may be utilized to predict measurements (e.g., electrode and sensor location measurements) given the current predicted state to produce a distribution of predicted measurements having a mean and covariance. Once the measurements are predicted, they may be compared with the actual measurements. A difference between the predicted measurements and actual measurements may be utilized to correct the current predicted state at box 316 of the flow diagram. Once the current state is corrected, outliers may, in an embodiment, be identified and removed from the current state at box 318 of the flow diagram. At this point a new state distribution is generated for the current update (e.g., time step). From the state distribution, electrode locations may be computed at box 320 of the flow diagram. Additionally, the various parameters (e.g., state variables) of the various models may be updated based on the new state distribution.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for estimating locations of electrodes based on a utilizing a system model has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method for use in predicting impedance measurements and identifying a location of a medical device, comprising:

driving a plurality of surface patch electrodes associated with a three-dimensional space to generate an impedance field in the three-dimensional space;

obtaining impedance measurements for one or more electrodes, separate from the surface patch electrodes, disposed within the three-dimensional space in response to the driving of the plurality of surface path electrodes; and mapping independent impedance potential fields of a portion of the plurality of surface patch electrodes that are non-driven to the impedance measurements to generate an impedance model of the impedance field;

receiving a predicted location of a catheter electrode from a catheter model that models a shape of a catheter in the three-dimensional space;

generating predicted impedance values for the predicted location of the catheter electrode in the three-dimensional space using the impedance model, wherein the predicted location of the catheter electrode is received from the catheter model;

obtaining measured impedance values for the catheter electrode as disposed in the three-dimensional space;

based on the predicted impedance values and the measured impedance values, generating calculated impedance values for the catheter electrode in the three-dimensional space;

updating the impedance model of the impedance field based on the predicted impedance values and the measured impedance values, wherein the updated impedance model is subsequently utilized to generate subsequent predicted impedance values for a predicted location of the catheter electrode, wherein the above steps of the method are performed without transformation from impedance measurements to a magnetic-based coordinate system; and outputting a location of the catheter electrode generated based on the calculated impedance values to a display.

2. The method of claim 1, wherein updating the impedance model of the impedance field based on the predicted impedance values and the measured impedance values includes updating definitions of the independent impedance potential fields.

3. The method of claim 1, wherein individual pairs of the plurality of surface patch electrodes are driven to generate the impedance field and the independent impedance potential fields extend between non-driven pairs of the plurality of surface patch electrodes.

4. The method of claim 1, wherein the mapping of the independent impedance potential fields further comprises:
defining each independent impedance potential field as a linear combination of basis functions, wherein each basis function comprises a weighting factor.

5. The method of claim 4, further comprising:
updating weighting factors of the basis functions based on the predicted impedance values and measured impedance values for the catheter electrode.

6. The method of claim 4, wherein the basis functions are constrained to obey Kirchoff's voltage law.

7. The method of claim 4, wherein the defining each independent impedance potential field further comprises:
adding an error term to the linear combination of basis functions.

8. The method of claim 7, wherein the error term comprises at least one of a distant dependent modeling error and a respiration dependent modeling error.

9. The method of claim 1, wherein the independent impedance potential fields comprise state variables.

10. The method of claim 9, wherein a Kalman Filter is used to infer the state variables.

11. The method of claim 9, wherein the Kalman Filter updates the state variables based on the predicted impedance values and measured impedance values for the catheter electrode.

12. The method of claim 1, wherein a number of the driven patch pairs exceeds a number of independent impedance potential fields.

13. A system for predicting impedance measurements and identifying a location of a medical device, comprising:
a catheter having a catheter electrode;
a medical positioning system configured to:
drive a plurality of surface patch electrodes associated with a three-dimensional space to generate an impedance field in the three-dimensional space; and
measure impedance responses of electrodes, separate from the surface patch electrodes, in the three-dimensional space;
a processor and memory for storing non-transitory computer readable instructions to:
obtain impedance measurements for electrodes disposed in the three-dimensional space from the medical positioning system; and
map independent impedance potential fields of a portion of the plurality of surface patch electrodes that are non-driven to the impedance measurements to generate an impedance model of the impedance field;
access a catheter model defining the catheter including the catheter electrode;
execute the catheter model to generate a predicted location of the catheter electrode;
generate predicted impedance values for the predicted location of a catheter electrode in the three-dimensional space using the impedance model, wherein the predicted location of the catheter electrode is provided by the catheter model;
obtain measured impedance values for the catheter electrode disposed in the three-dimensional space; and
generate calculated impedance values for the catheter electrode using the predicted impedance values and the measured impedance values; and
update the impedance model of the impedance field based on the predicted impedance values and the measured impedance values, wherein the updated impedance model is subsequently utilized to generate subsequent predicted impedance values for a predicted location of the catheter electrode, and the processor operates the above steps without transformation from impedance measurements to a magnetic-based coordinate system; and
a display configured to display a location of the catheter electrode generated using the calculated impedance values.

14. The system of claim 13, wherein the medical positioning system is configured to drive individual pairs of the plurality of surface patch electrodes to generate the impedance field.

15. The system of claim 14, wherein the non-transitory computer-readable medium further comprises instructions to map independent impedance potential fields between non-driven pairs of the plurality of surface patch electrodes to the impedance measurements.

16. The system of claim 13, wherein the instructions stored by the non-transitory computer-readable medium to update the impedance model of the impedance field based on the predicted impedance values and the measured impedance values further comprises instructions to update definitions of the independent impedance potential fields using the predicted impedance values and the measured impedance values.

17. The system of claim 16, wherein the non-transitory computer-readable medium further comprises instructions to update weighting factors of basis functions defining the independent impedance potential fields.

18. The system of claim 13, wherein the non-transitory computer-readable medium further comprises instructions to implement a Kalman Filter to infer state variables, wherein the independent impedance potential fields comprise state variables.

* * * * *